(12) United States Patent
Le Roy et al.

(10) Patent No.: US 7,488,937 B2
(45) Date of Patent: Feb. 10, 2009

(54) METHOD AND APPARATUS FOR THE IMPROVEMENT OF MATERIAL/VOLTAGE CONTRAST

(75) Inventors: Erwan Le Roy, Newark, CA (US); William B. Thompson, Los Altos, CA (US)

(73) Assignee: Credence Systems Corp, Milpitas, CA (US)

( * ) Notice: Subject to any disclaimer, the term of this patent is extended or adjusted under 35 U.S.C. 154(b) by 346 days.

(21) Appl. No.: 11/252,139

(22) Filed: Oct. 17, 2005

(65) Prior Publication Data

US 2006/0037182 A1 Feb. 23, 2006

Related U.S. Application Data

(62) Division of application No. 11/212,832, filed on Aug. 25, 2005, which is a division of application No. 10/789,336, filed on Feb. 27, 2004, now Pat. No. 6,958,248.

(60) Provisional application No. 60/450,636, filed on Feb. 28, 2003, provisional application No. 60/523,063, filed on Nov. 18, 2003.

(51) Int. Cl.
*H01L 21/00* (2006.01)
(52) U.S. Cl. ............. 250/310; 250/492.1; 438/10; 438/18; 716/20; 716/21; 257/E21.521
(58) Field of Classification Search ............. 438/10, 438/17, 18; 250/310, 492.1; 29/25.01; 716/20, 716/21
See application file for complete search history.

(56) References Cited

U.S. PATENT DOCUMENTS

| | | | |
|---|---|---|---|
| 6,372,627 B1 * | 4/2002 | Ring et al. | 438/622 |
| 6,955,930 B2 * | 10/2005 | Le Roy et al. | 438/16 |
| 2002/0151091 A1 * | 10/2002 | Shaw et al. | 438/14 |

* cited by examiner

*Primary Examiner*—Alexander G Ghyka
(74) *Attorney, Agent, or Firm*—Deborah W. Wenocur

(57) ABSTRACT

A method and system for registering a CAD layout to a Focused Ion Beam image for through-the-substrate probing, without using an optical image and without requiring biasing, includes an improved method of trench endpointing during the FIB milling operation with a low beam energy. The method further includes removal of Ga at the trench floor using $XeF_2$, as well as the deposition of an insulating layer onto the trench floor.

25 Claims, 21 Drawing Sheets

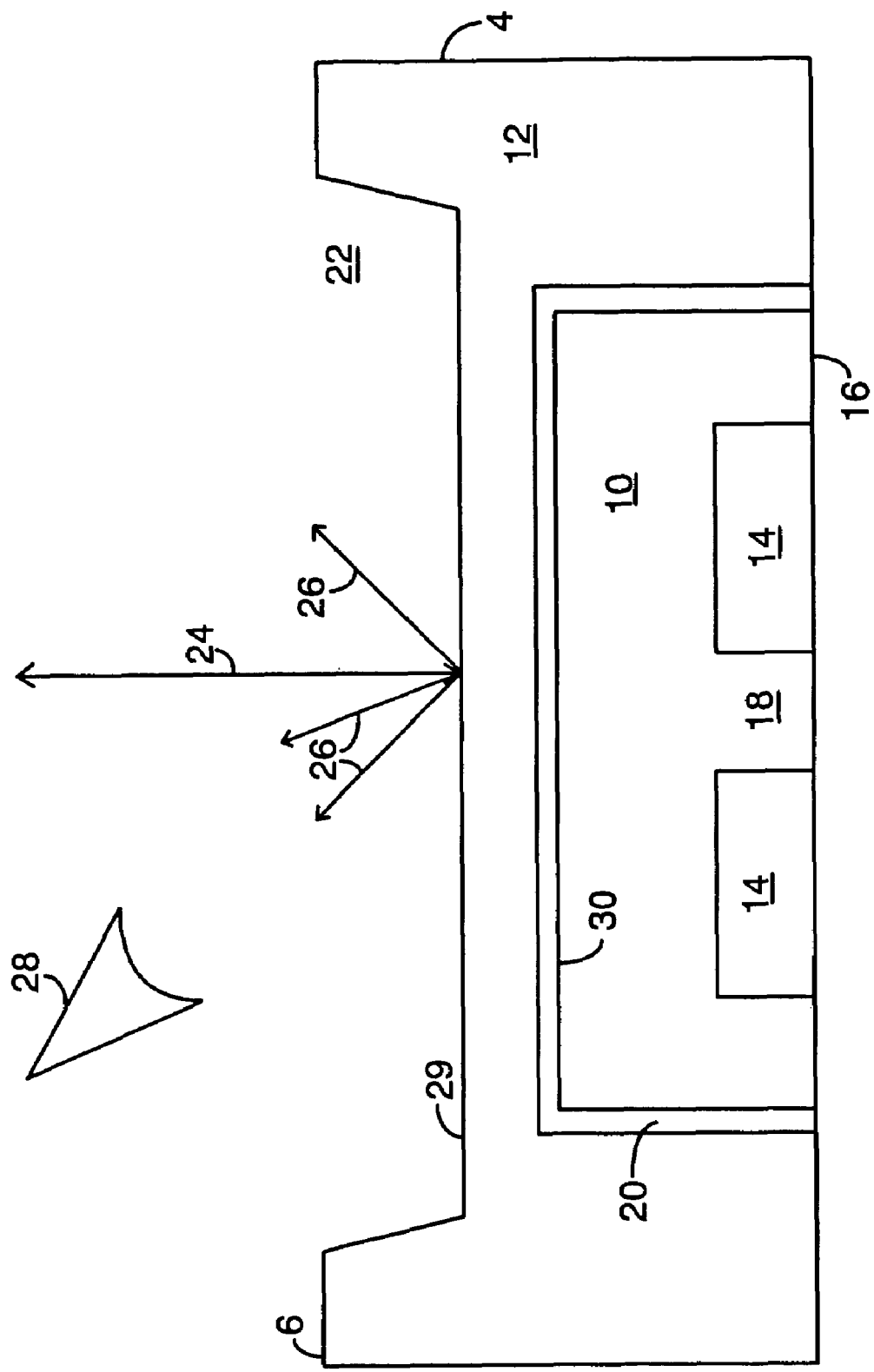

METHOD AND APPARATUS FOR THE IMPROVEMENT OF MATERIAL/VOLTAGE CONTRAST

CROSS REFERENCE TO RELATED APPLICATIONS

This application is a divisional of copending U.S. application Ser. No. 11/212,832, filed on Aug. 25, 2005, and claims priority thereto. application Ser. No. 11/212,832 is a divisional of Ser. No. 10/789,336, filed on Feb. 27, 2004, now U.S. Pat. No. 6,958,248 to be issued, and claims priority thereto. The specification of U.S. application Ser. No. 10/789,336 is hereby incorporated by reference.

This application is further related to U.S. Provisional Applications No. 60/450,636 by Erwan Le Roy and William Thompson, filed Feb. 28, 2003, and No. 60/523,063 by Erwan Le Roy and William Thompson, filed Nov. 18, 2003, and claims priority to both of these provisional applications.

This application is further related to commonly owned U.S. application Ser. No. 10/758,146 entitled "METHOD AND SYSTEM FOR INTEGRATED CIRCUIT BACKSIDE NAVIGATION", filed Jan. 14, 2004.

BACKGROUND OF THE INVENTION

As IC technology advances and device dimensions decrease while circuit speeds increase, packaging and diagnostic techniques have advanced accordingly. Methods for modification and editing of circuits and devices have undergone dramatic changes, due in part to two factors. The stacking of increasingly large numbers of metal layers has limited the access to lower metal layers from the wafer frontside. In addition, the widespread use of flipchip mounting, wherein the IC is mounted face down on a packaging substrate, leaving only the backside of the chip exposed, precludes front side access to the chip. As a result of these aforementioned factors, backside signal measurement, editing, and modification of IC's has become increasingly important, using such techniques as Focused Ion Beam (FIB). The use of FIB in backside editing and repair of IC's is described by C. G. Talbot et al in commonly owned U.S. Pat. No. 6,518,571, issued Feb. 11, 2003, and by T. Lundquist et al in commonly owned U.S. patent application Ser. No. 09/738,826, filed on Dec. 15, 2000, both of which are hereby incorporated in their entirety by reference. The technique includes: 1) the global thinning of the die, 2) the optional cutting of a coarse trench (by methods such as Laser Chemical Etching or FIB), 3) milling of a smaller trench within the LCE trench to within one to a few microns of the active diffusion regions (by chemically assisted FIB), 4) FIB sputter removal or fine chemically assisted FIB milling between active diffusion regions or active devices to provide access to one or more circuit elements, and finally 5) probing, cutting, depositing, or connecting signal paths as required.

Precise endpoint control over the milling of the small trench is critical to avoid damaging of active diffusion regions. Various methods of trench endpointing have been reported in the literature. By way of example, Winer et al, in U.S. Pat. No. 5,948,217 disclose a method of endpointing which is sensitive to changes in diffusion region doping chemistry, but which requires biasing of diffused regions such as n-wells with respect to the substrate.

A challenge in backside editing is navigation, i.e., locating the exact circuit node where a modification or repair is needed. To effectively and accurately access the circuit elements to be modified, both the milling of the small trench and the fine FIB milling must be accurately positioned and registered with respect to the circuit design (CAD) and circuit elements. Various techniques have been used to create a backside image, which can be matched to the CAD layout of the chip.

A prior method for registration is IR imaging through the silicon. The IR light can pass through silicon, and optical information about the location on the chip, as well as about remaining thickness of silicon (i.e., endpoint information) is provided. This method is described in previously cited U.S. Pat. No. 6,518,571, and by E. Le Roy et al in commonly owned U.S. patent application Ser. No. 10/161,272 filed on May 30, 2002. An IR imaging and navigation system has been combined with FIB in an apparatus called IDS OptiFIB, made by NPTest, LLC. The resolution of IR imaging is limited to its wavelength, but use of an imaging process algorithm should improve corresponding CAD alignment accuracy to a fraction of one wavelength. Use of the IDS OptiFIB for CAD alignment is described in commonly owned U.S. patent application Ser. No. 10/159,527 by M. Sengupta el al, filed May 30, 2001, which is hereby incorporated in its entirety by reference.

A method known as voltage contrast, which does not utilize IR and which has been used in front-side imaging, has been recently applied in backside navigation, as described in the commonly owned U.S. patent application Ser. No. 10/274,431 by C. C. Tsao et al, filed Oct. 17, 2002, which is hereby incorporated in its entirety by reference. This method includes the biasing of n-well implanted regions with respect to the p-substrate, and shows a clear backside FIB image of the n-well regions which can be used for registration to the CAD design. However, this prior method is not effective in imaging non-biased regions. Additionally, operational complexity is introduced by this method, since a special socket for each particular device and the interconnect board to the electrical bias is required to provide the bias, and an increased knowledge level is required to know which pins should be biased relative to which others. An alternative method for registering the CAD to the FIB image which did not require biasing and which could distinguish between surface and buried material regions, as well as a method to ensure accurate endpoint detection in the small trench milling, would be advantageous in through the substrate probing and circuit modification and other modifications for flip-chip mounted IC's and properly prepared wire-bonded IC's, and could additionally be utilized in obtaining vertical doping profiles for n-well characterization for failure analysis, and possibly for p-well characterization.

SUMMARY OF THE INVENTION

It is therefore an object of this invention to provide an improved method and system for registering a CAD to the FIB image for through-the-substrate probing, without using an optical image and without requiring biasing.

It is a further object of this invention to provide an improved method of trench endpointing during the FIB milling operation with a low beam energy.

It is a still further object of this invention to provide a method for imaging of vertical doping profiles.

These objectives are met by a process and a system for implementing the process, including the use of low ion beam energies, removing the ion beam-deposited Ga layer using $XeF_2$, depositing a high quality insulating anti-reflection coating at low beam energy, and observing secondary electron fluctuation induced by an underneath material- or potential-contrast. This inventive process provides an enhanced voltage contrast between structures which is observable on the FIB image.

BRIEF DESCRIPTION OF THE DRAWINGS

FIG. 1b illustrates the wafer of FIG. 1a having a backside ion-beam milled trench therein.

FIG. 7b is the corresponding CAD layout to FIG. 7a.

DETAILED DESCRIPTION OF THE INVENTION

"The present invention provides a method and a system for implementing the method, for inducing steady state voltage contrast between regions on an IC chip backside, so as to observe structures on a FIB image. The inventive method enables the FIB imaging without necessity of external voltage bias of regions such as the n-well regions. Voltage contrast induced without external bias is hereinafter termed "inherent voltage contrast". It further enables the use of the FIB ion beam to map the wafer from the backside, i.e., to locate positions of various materials and diffusion regions. The method is believed to be based on differential capacitive characteristics of an MOS-like structure (M=Induced Surface Conductive layer created by the beam interaction with an oxide; O=oxide; S=underlying semiconductor) which affect the secondary electron emission from the substrate. The surface of the exposed wafer backside acts as the top plate of a capacitor, a layer or feature below the surface acts as the bottom plate of the capacitor, and the intervening material or materials such as silicon or silicon oxide acts as the dielectric between the capacitor plates. The surface potential in such a capacitive situation is dependent on the potential of the material below, the local dose, the secondary electron emission coefficient of the insulator, the dielectric film quality, including trapped charge density and oxide/semiconductor interface charge density, and leakage currents (surface current and leakage in the capacitor). This in turn affects the secondary emission current, which is detected to form the FIB image. The differential in surface potential above different regions such as differing exposed or buried dopant types or concentrations, or different materials, provides a map on the FIB image. "The experimental results reported herein were performed using an NPTest OptiFib system. Note that the OptiFIB inherently includes a coaxial photon ion column, which provides uniform illumination to the sample. Flip-chip packaged die, having CMOS devices in a p-doped substrate, were globally thinned to less than 100 microns, and an Anti-Reflective Coating (ARC) deposited on the silicon. Die were installed into the FIB chamber, and all pins grounded. At the location where the trench was to be milled, the ARC was removed and the silicon surface was cleaned using Ga ion sputtering and ethylene di-iodide enhanced etching."

Figure 1A:
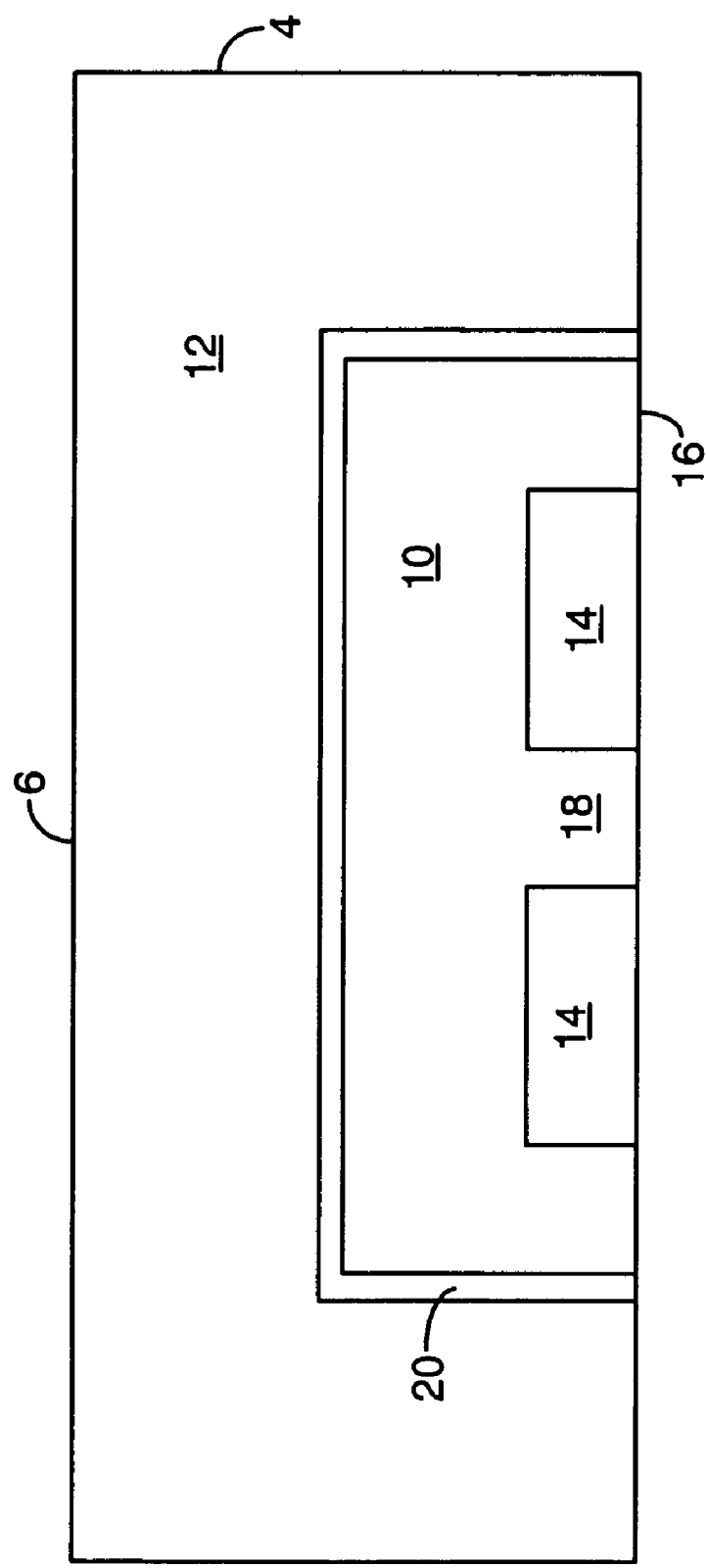
FIG. 1a illustrates a portion of a thinned semiconductor wafer having devices therein.

FIG. 1a shows a portion of a thinned wafer 4 with back surface 6 and with diffused regions therein. N-well region 10 is diffused into p-substrate 12. Active p-regions 14 at front surface 16 of n-well 10 have gate/channel region 18 therebetween. N-well 10 and p-substrate 12 are separated by depletion region 20, which is depleted of mobile carriers.

FIG. 1b shows the wafer 4 of FIG. 1a, with ion beam-milled trench region 22 above n-well 10 and p-substrate 12. FIB ion beam 24 (which is comprised of positive Ga ions) is scanned across trench region 22 at approximately 60 frames/sec or 30,000 lines/sec. Secondary electrons 26 are emitted, which are detected by detector 28, a scintillator/PMT assembly by way of example. The scintillator/PMT assembly detector subsystem is described in commonly owned U.S. patent application Ser. No. 09/675,981 by L. Wang et al, filed Sep. 29, 200, which is hereby incorporated in its entirety by reference. The scintillator/PMT assembly shows higher secondary electron emission regions as brighter than lower secondary emission regions.

A transient voltage contrast effect is seen as ion beam 24 mills trench region 22 such that trench floor 29 approaches sufficiently close (between 1 and 5 microns) to boundary 30 of n-well region 10. The n-well region appears brighter than the p-substrate as it is first contacted, then returns to being dark after a few imaging scans of the ion beam. By way of example, at beam current of 12 nA with a Field of View (FOV) of 350 $um^2$, the transition from bright to dark occurs after 2 imaging scans. An aspect of the present invention is the use of a low beam energy, 15 keV by way of example, to enhance this visual transient voltage contrast effect. It is believed that the lowered beam energy decreases the thickness of the ion-beam induced amorphous layer at the trench floor, and that the higher doping density of the n-well region is observed visually as a higher secondary electron yield than that of the p-substrate. The rapid transition of the n-well region from bright to dark is thought to be due to the ionization energy difference between n and p regions, created by the electric field induced by the p/n junction built-in potential. The secondary electrons emitted from the p-substrate requires less energy to reach the vacuum level than from the n-wells. The n-wells will then appear dark compared to the p-substrate.

The appearance of the transient visual voltage contrast effect can be used as a visual endpoint for use in navigating across most regions through the wafer backside.

The present invention further demonstrates a method for enabling a steady state voltage contrast to be observable on a FIB image which can be utilized to register the CAD to the FIB image without use of IR imaging, and without requiring biasing of the sample. This method includes the use of $XeF_2$ to remove the implanted Ga layer from the trench floor, as well as the deposition of a high quality insulator layer at low beam energy.

Figure 2:
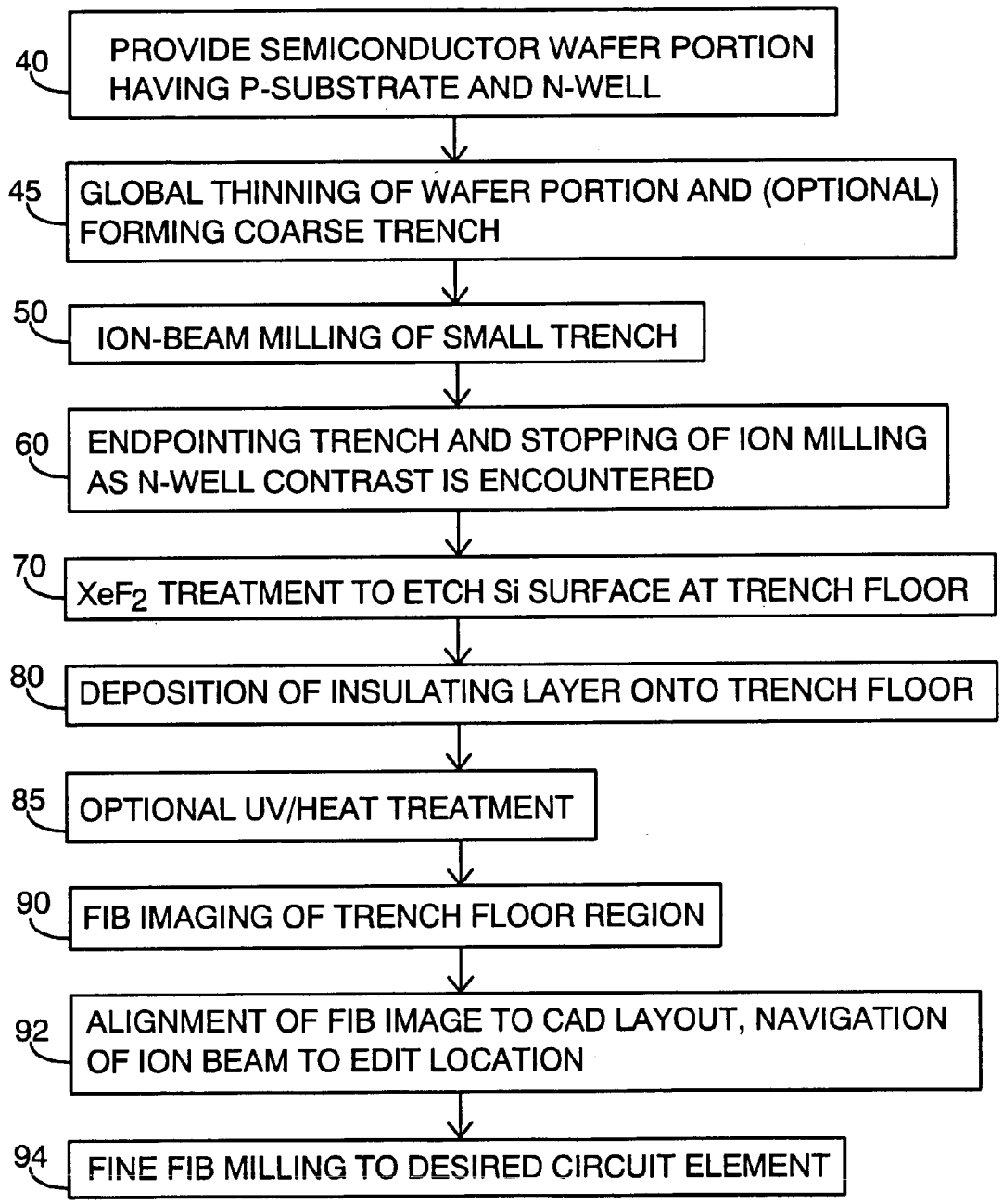
FIG. 2 is a flow chart illustrating the inventive method.

An embodiment of the invention is described below and illustrated in flow-chart form in FIG. 2. It is to be understood that the embodiment is described showing an illustrative structure comprising an n-well region in a p-substrate, but that the method can be applied to other structures without departing from the inventive concept.

In step 40, semiconductor wafer portion 4 is provided having p-substrate 12 with n-well 10 therein.

In step 45, the wafer portion 4 is globally thinned and a coarse trench cut using standard techniques.

In step 50, trench 22 is ion-beam milled using FIB ion beam 24.

In step 60, trench 22 is endpointed and ion milling stopped as the n-well contrast is encountered, which for most IC designs is approximately 2 to 4 microns from the top of the silicon or ILD0.

In step 70, implanted Ga at trench floor 29 is removed by exposing trench floor 29 to $XeF_2$ which spontaneously etches the surface of the Si.

In step 80, a high quality insulating layer, typically $SiO_x$, is deposited at low beam energy of approximately 5 to 15 keV onto trench floor 29. Optional illumination (which may be at IR wavelengths) of the surface during insulator deposition may be utilized.

In step 85, an optional UV treatment and/or heat treatment is performed to improve the oxide quality.

In step 90, the FIB ion beam is scanned across trench region 22 and the resulting secondary electrons are detected to form a FIB image. In an embodiment, imaging is performed at a beam current of 30 keV, and a beam current of 500 pA or greater. Lower values are expected to be usable as insulating layer quality is optimized.

In step 92, the FIB image is aligned to the CAD layout and the ion beam is navigated to the precise location where editing is required.

In step 94, fine FIB milling to the desired circuit element is performed.

The global thinning and coarse trench cutting in step 45 and the ion milling of trench 22 in step 50 may be accomplished using prior techniques such as those described in commonly owned U.S. patent application Ser. No. 10/274,431 filed Oct. 17, 2002, which is hereby incorporated in its entirety by reference.

The ion beam typically used in the milling of the small trench 22 (the trench typically has dimensions of about 100 microns squared to 250 microns squared), is in the energy range between 25-50 KeV, most usually 30 KeV, with a beam current in the range between 10-25 nA, most usually approximately 12-20 nA. The ion milling is generally performed in the presence of a chemical such as $XeF_2$ or $Cl_2$ for assisting in FIB material removal.

Step 60 of the present invention provides a novel method for obtaining a precise visual endpoint during the ion milling of trench 22. This visual endpoint is seen as the trench floor 29 reaches the boundary 95 between the p-substrate 12 and n-well 10. The endpointing method uses a reduced FIB ion beam voltage as the n-well is approached. At approximately 10 microns from the n-well boundary 95, which is determined by fringe contrast in the IR imaging, as described in earlier cited U.S. patent application Ser. No. 10/161,272 or using a programmable script which predicts thickness of removed silicon according to calculations of removal rate, the FIB ion beam parameters are lowered to an energy in the range between 10-15 KeV and a current of preferably 4-25 nA but extendable to a range of 2-25 nA and believed to be viable in the range of 0.4 to 50 nA. A preferred embodiment utilizes a beam current of 4 nA and a beam energy of 15 keV. These parameters have been determined to optimize the contrast, while not excessively degrading resolution of the visual image which appears as the n-well boundary is approached. The beam current density at these current and voltage values, at the standard field of view of less than 150 $um^2$, is approximately 0.2 $pA/um^2$ for a pressure of 2×10−5 Torr.

It is believed that the low beam energy minimizes the depth of an implanted Ga-induced amorphous layer formed at the trench floor 29, which allows for a clear materials contrast to be seen. The implanted Ga range is calculated to be approximately linear, with a depth (corresponding approximately to the amorphous layer thickness) of about 15 nm for 15 keV beam energy, and a depth of about 25 nm for 30 keV energy. The implantation of the Ga, however, is offset by the etch/milling rate of the Si, therefore during the chemically-enhanced milling the actual amorphous layer thickness is lower than the above. The beam current density must be held at a sufficiently low level to maintain a sufficiently high $XeF_2$-induced Si etch rate to prevent a build-up of a thick layer of implanted Ga at the trench floor. However, it must be sufficiently high to prevent an excessive spontaneous reaction of $XeF_2$ with Si, which would increase the topography of the Si surface and it is believed would increase the density of surface states. The beam current density must therefore be optimized to avoid either of these effects. A Ga implanted layer at the surface of the n-well would cause the formation of an amorphous surface which would reduce or prevent the visibility of a direct materials contrast between the n-well region and the p-substrate.

According to the present invention, the FIB ion beam milling is stopped when the visual endpoint from the transient voltage contrast described above is encountered Steps 70 and 80 are directed to stabilization of the voltage contrast between the n-well regions and the p-substrate regions in order to enable the formation of an optimized FIB image. This image may be registered to the CAD layout of the chip so as to navigate accurately for editing. As described above, the voltage contrast as the n-well is encountered is transient: i.e., the n-well regions appear bright at first, but darken after only a few imaging scans of the FIB beam. This is thought to be due to the implanted Ga from the imaging scans, which is not etched away since the $XeF_2$ flow is discontinued during the imaging scans, to avoid further etching and milling during imaging.

"The formation of a steady state voltage contrast according to the present invention requires a substantially crystalline, non-amorphized Si surface at the trench floor (which inherently must be substantially uniform), and a high-quality insulating layer (which also inherently must be substantially uniform) thereon. The combination of these two components enables the imaging of a capacitively-induced (from an MOS-like structure in depletion mode) voltage contrast between n-well regions and p-substrate regions."

In step 70, $XeF_2$ is utilized to etch away residual implanted Ga, along with the upper non-crystalline Si layer, leaving a high quality crystalline Si surface which is substantially free of Ga.

$XeF_2$ etches silicon spontaneously at a high rate of about 24000 A/min at room temperature and partial pressure of 3 e15 molecules/cm$^3$ of $XeF_2$, or about $8 \times 10^{-2}$ Torr. This effect is described by J. W. Coburn and H. F. Winters in *J. Appl. Physics* 50 (1979), 3189. It creates an $SiF_x$ layer and produces volatile etch products with low or even negative binding energies, which comprise mainly $SiF_4$, but also include $Si_2F_6$ and $Si_3F_8$. It is believed that reactions within the $SiF_x$ layer continue to create etch products after the $XeF_2$ exposure is terminated, and also that the Ga leaves the surface as a member of the $SiF_x$ products.

Figure 3:
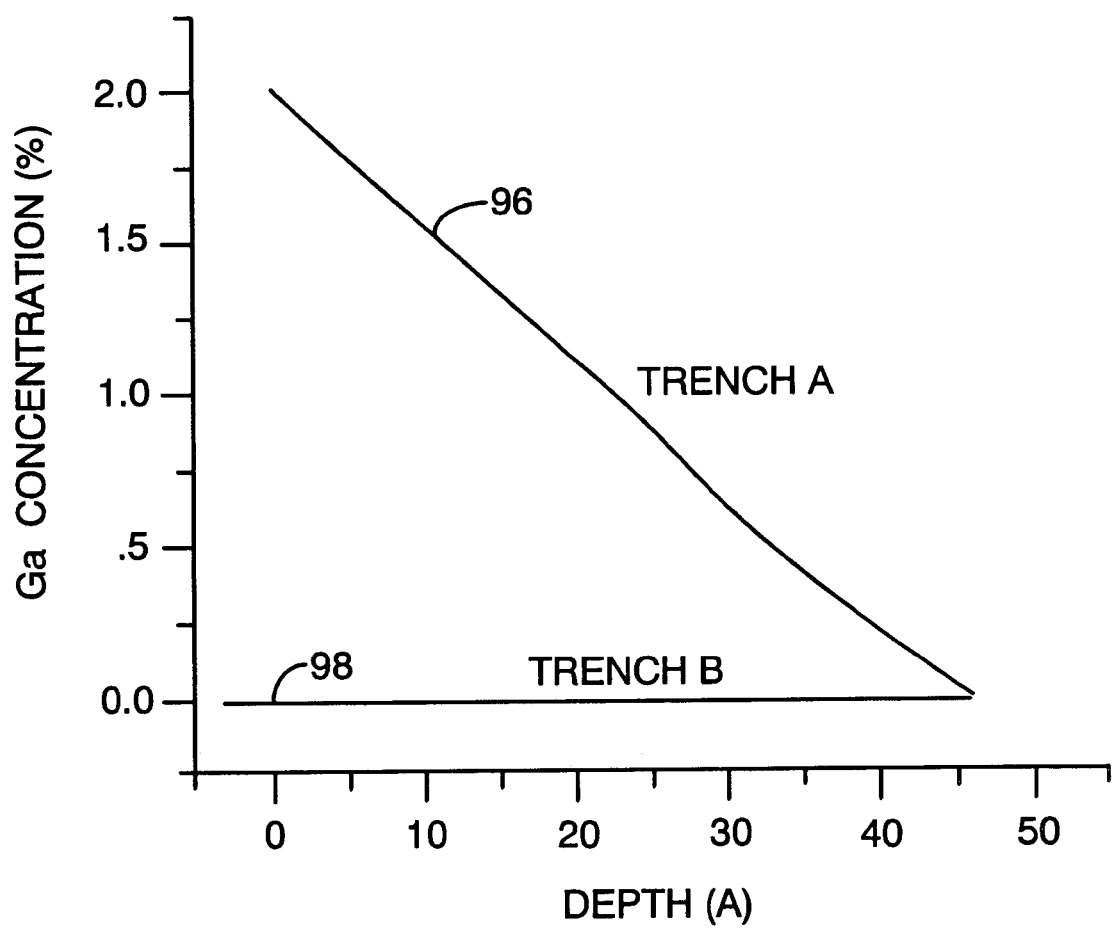
FIG. 3 is a graph of Auger results from a trench floor with and without $XeF_2$ treatment.

FIG. 3 shows Auger depth profiles of Ga concentration at a first trench floor (curve 96) having no $XeF_2$ treatment after ion milling is stopped, and equivalent Auger results from a similar second trench floor (curve 98) having 14 seconds $XeF_2$ exposure after ion milling is stopped. For this example, the trenches were 100 um$^2$ in area, were ion milled for 5 minutes using a $XeF_2$ chamber pressure of $2 \times 10^{-5}$ Torr. Ga is detected at the first trench floor down to a depth of approximately 45 Angstroms, whereas no Ga is detected at the second trench floor, showing the effectiveness of the $XeF_2$ in etching away the surface Ga-containing layer. Based on the aforementioned Auger results, the spontaneous etching removed at least 45 A in 14 seconds. The etch rate under these conditions is about 193 A/min.

According to an embodiment of the present invention, step 70 comprises blanking off the FIB ion beam as soon as the voltage contrast endpoint is reached, and maintaining a chamber pressure of 2 to $5 \times 10^{-5}$ Torr of $XeF_2$ for a time of 8-15 seconds, though the exposure time may be as short as 3 seconds. In a preferred embodiment, the chamber $XeF_2$ pressure is $2.8 \times 10^{-5}$ Torr, and the time is 10 seconds. The local $XeF_2$ pressure at the die is considerably higher, estimated to be at least $8 \times 10^{-4}$ Torr, possibly as high as in the $10^{-2}$ Torr range. This estimate is based on the known facts that the $XeF_2$ etch rate of silicon is linear below 0.5 Torr $XeF_2$ pressure, and that the etch rate at about 0.1 Torr is 24000 A/min.

Figure 4:
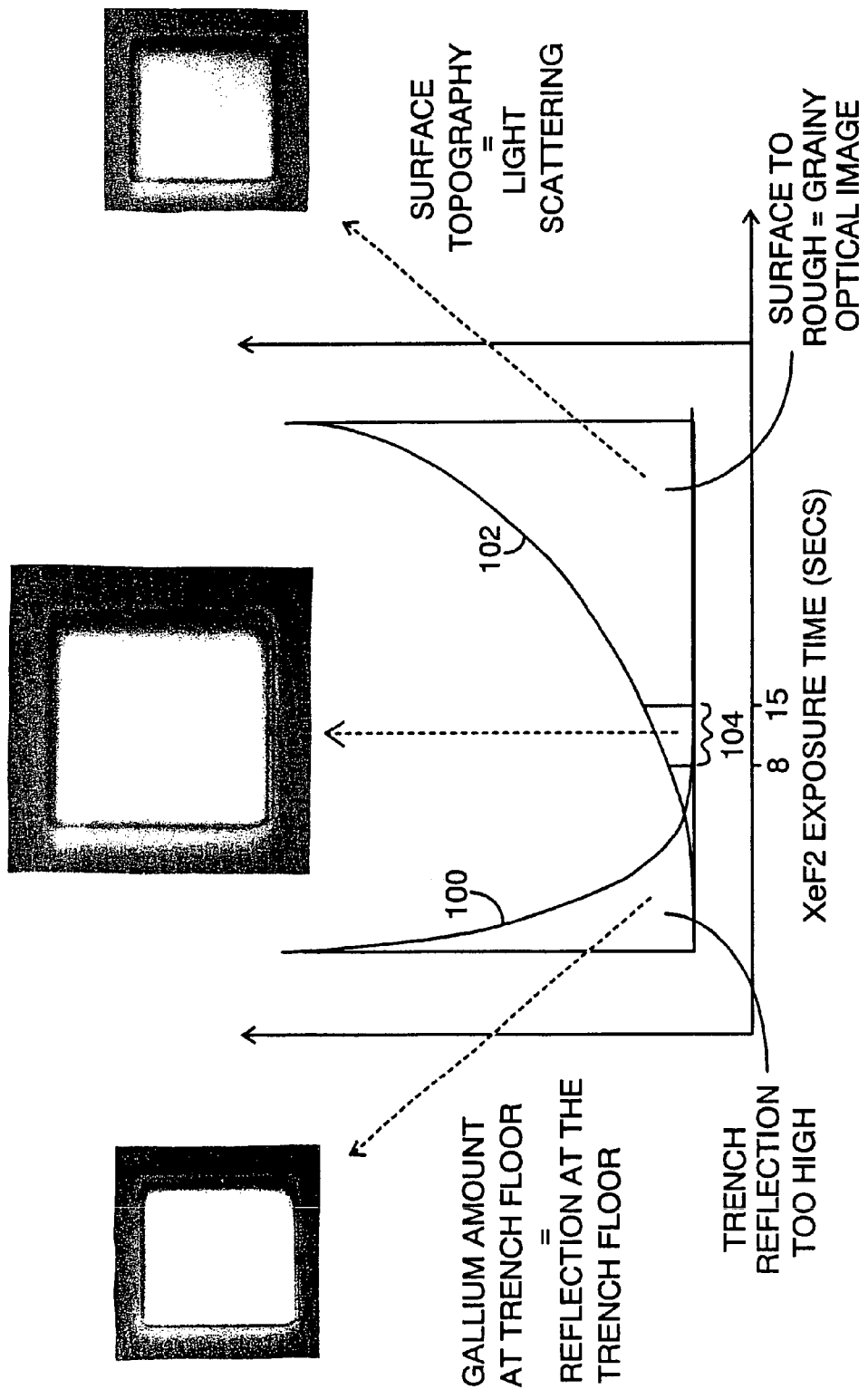
FIG. 4 is a graph of reflectance at a trench floor and of light scattering from the trench floor as a function of $XeF_2$ exposure time.

The optimum range is determined, at the lower end, by substantially complete removal of the implanted Ga. The removal of Ga is confirmed by low light reflectance at the trench floor. The higher end of the optimum range is determined by maintaining a sufficiently smooth surface topography, as confirmed by light scattering. FIG. 4 illustrates the aforementioned factors, and shows the optimal range according to the $XeF_2$ parameters described above to be 8-15 seconds exposure. Curve 100 shows reflectance decreasing with longer exposure, and curve 102 shows light scattering (as measured qualitatively according to the granularity of the optical image) increasing with longer exposure. Range 104 falls near the minimum of both light reflectivity and light scattering.

Following the $XeF_2$ exposure, the $XeF_2$ flow is discontinued and the system pressure rapidly drops to its baseline level in the high $10^{-7}$ Torr-low $10^{-6}$ Torr range.

In step 80 a high quality insulating layer, typically $SiO_x$, is deposited by the FIB beam at low beam energy onto trench floor 29 immediately after the implanted Ga has been removed by the process of step 70. FIB oxide deposition parameters include introducing a partial pressure of a silicon oxide precursor, a silicon- and oxygen-containing compound such as Di-Butoxy-Di-Acetoxy-Silane (DBDAS). Other compounds which may be used for FIB oxide deposition include, but are not limited to: Tetraethoxysilane (TEOS), Tetramethylcyclotetrasiloxane (TMCTS), Octamethylcyclotetrasiloxane (OMCTS), Pentamethylcyclopentasiloxane (PMCPS), Dodecamethylcyclopentasiloxane (DMPS), and Tetrakis(dimethylsiloxy)silane (TDMSS). In a preferred embodiment, a partial pressure of about $2.5 \times 10^{-5}$ Torr of DBDAS is provided for about 35 minutes at room temperature.

In an embodiment of the present invention, approximately 120-140 nm oxide, with a preferred value of 130 nm, is deposited at a beam current density in the range of 0.02-0.2 pA/um$^2$ and a beam energy in the range of 5-15 keV, with preferred values of 4 nA beam current and 15 keV beam energy. This preferred oxide thickness is equivalent to the optimal Anti-Reflective Coating (ARC) thickness. The oxide layer will therefore hereinafter be referred to interchangeably as the ARC layer. Although in the embodiment disclosed, the ARC layer is deposited in situ in the IDS OpiFIB, it is to be understood that it may be deposited or grown in other tools, alone or in combination with the $XeF_2$ treatment. Other possible deposition methods include but are not limited to: low temperature PVD or CVD, or spin-on.

Figure 5:
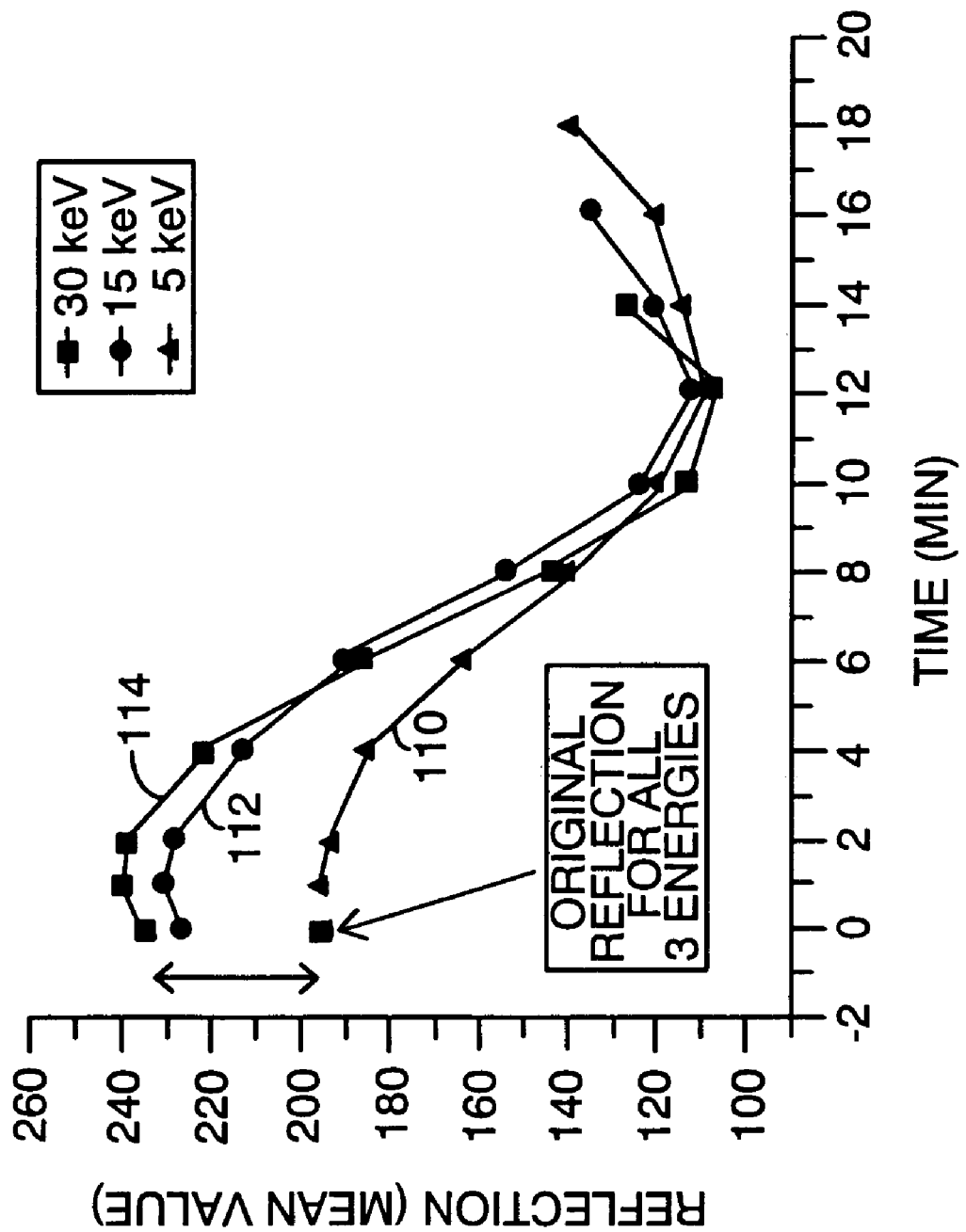
FIG. 5 is a graph of reflectance vs. time for oxide deposition at differing FIB beam energies.

FIG. 5 shows a graph of reflectance vs. time for oxide layer deposition at differing FIB ion beam deposition energies. Curve 10 shows results for 5 keV beam energy, curve 112 shows results for 15 keV beam energy, and curve 114 shows results for 30 keV beam energy. Mean reflectance value, measured on a gray scale from 0-256 using Photoshop software, for all three energies is approximately 195 at t=0, and passes through a minimum of approximately 115 at t=12 min, corresponding to about 130 nm oxide thickness for all three depositions. Reflectance immediately jumps upward for BE=15 keV and 30 keV until about t=2 min, corresponding to about 20 nm oxide thickness, then decreases to its minimum value at t=12 min. The initial jump in reflectance indicates that for 15 keV or greater, the first approximately 20 nm of oxide film is poor quality, believed to include Ga, Si, O, and C. This poor quality is substantiated by both the FIB image monitoring during deposition and by light reflection, both of which are dependent on the chemical structure and both of which indicate that the initial layer is rich in a metallic compound, of which Ga is the only metal present.

Figure 6:
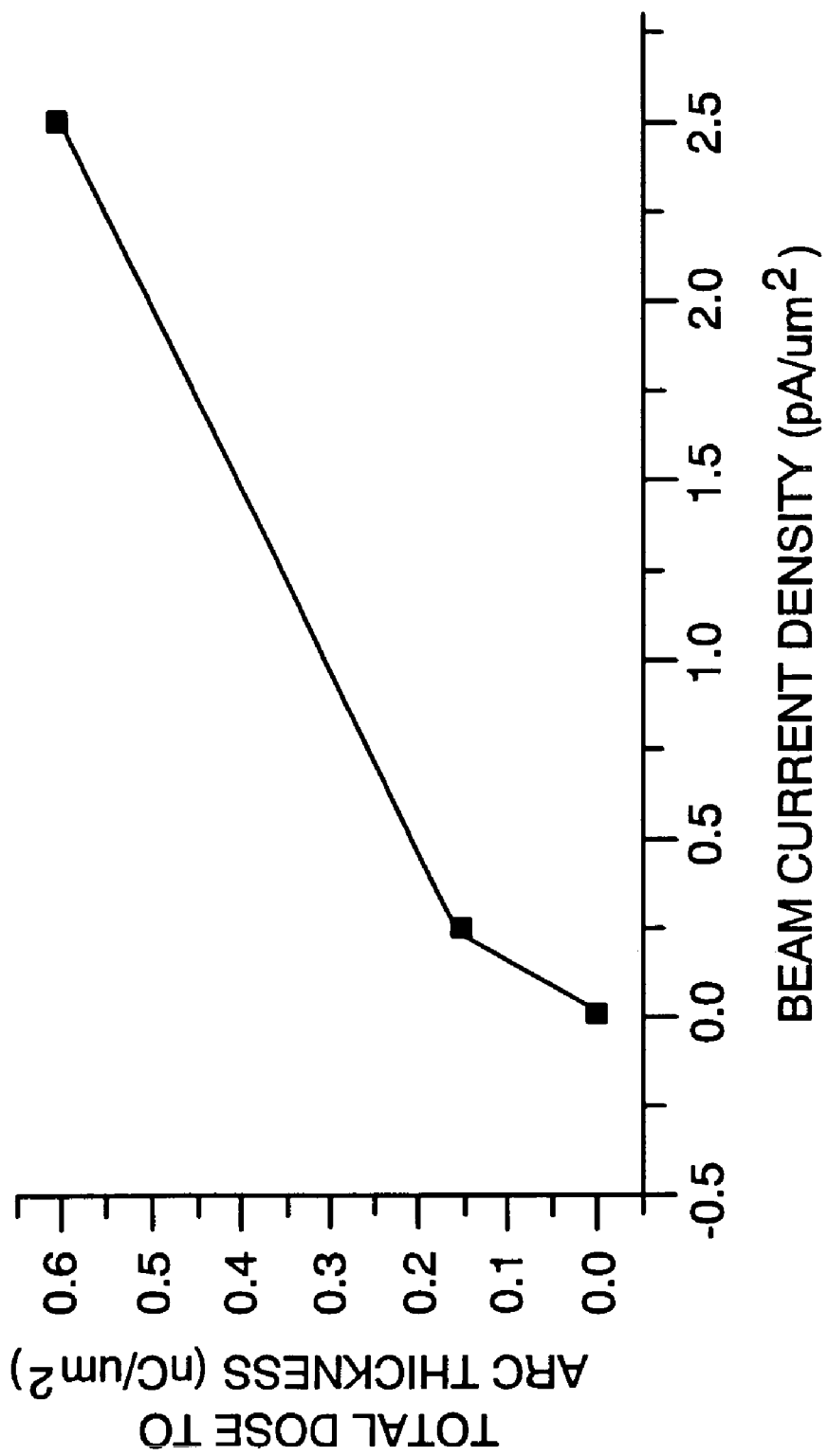
FIG. 6 is a graph of total dose to oxide layer thickness vs. beam current density during oxide deposition.

FIG. 6 shows a graph of total dose to oxide layer thickness (nC/um$^2$) vs. beam current density (pA/um$^2$) during oxide deposition. The best dose enhancement is seen at a low beam current density of 0.02 pA/um$^2$. This is believed to correspond to a smaller Ga concentration in the film.

Following deposition of the oxide film, DBDAS flow is discontinued and the chamber pumped down. In step 85 an optional heat treatment and/or UV treatment is performed to improve the oxide quality. A preferred embodiment utilizes a high power broadband light source, which provides UV, and a separate convective heat source at T=80 C, for 5 minutes-5 hours.

Figure 7A:
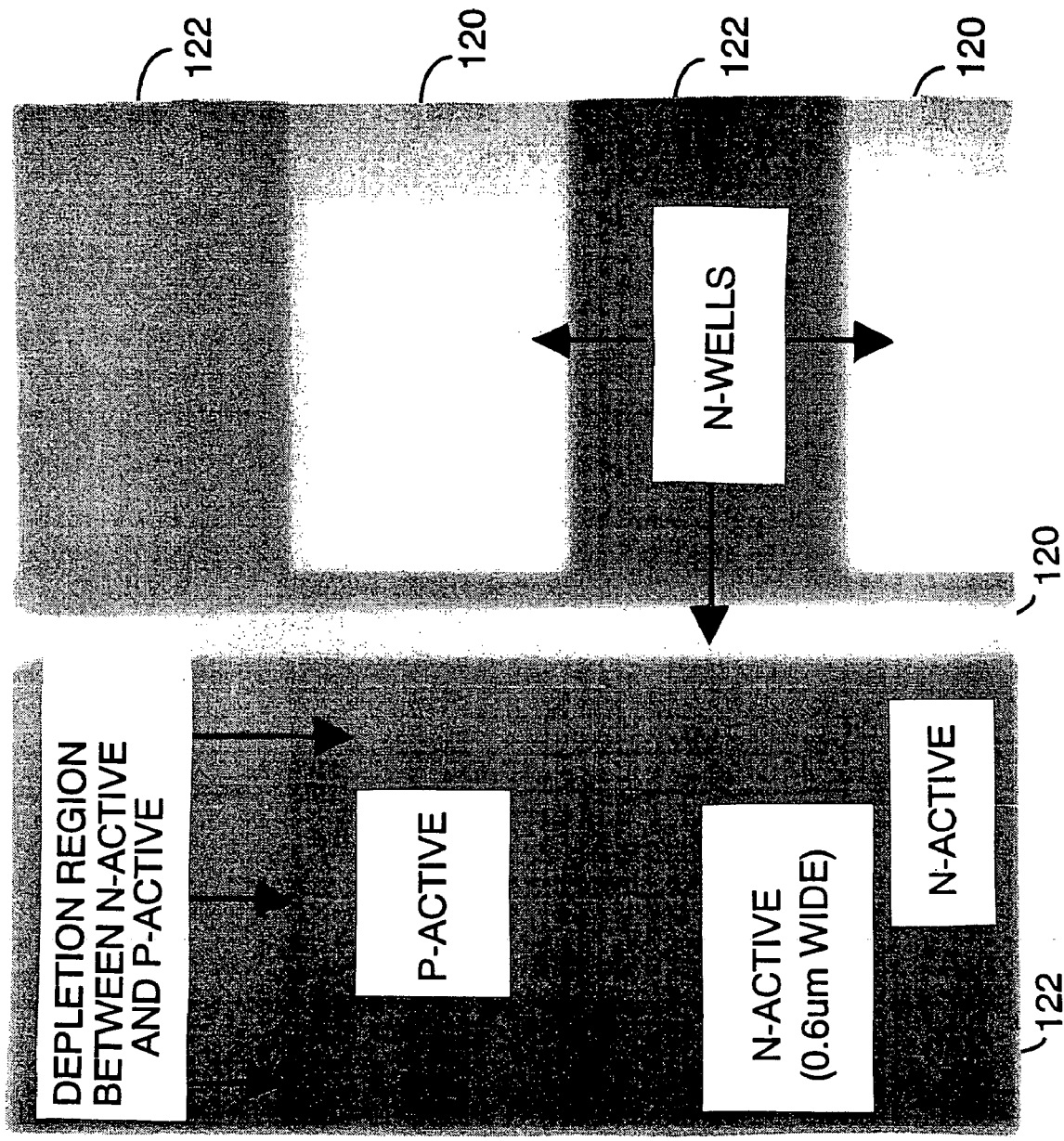
FIG. 7a is a voltage contrast image showing n-well and p-substrate regions.
Figure 7B:
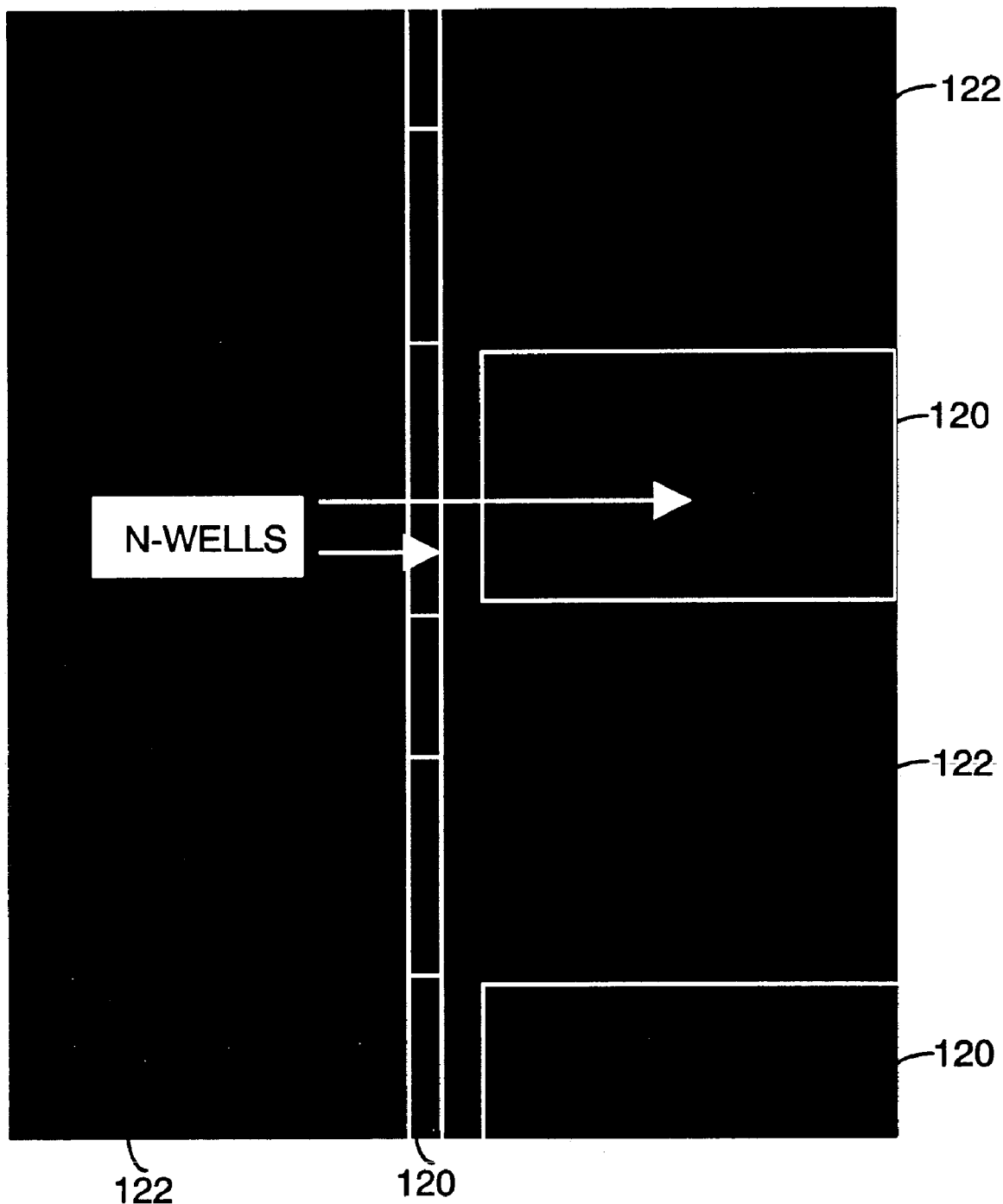

Step 90 comprises image scanning of the trench floor by the FIB ion beam. Techniques, apparatus, and controls for image scanning are described in "*Coaxial Ion-Photon System*" by C. C Tsao et al, Micro. Re. 41 (2001), pg. 1483, which is hereby incorporated by reference. During imaging, the sample is grounded. According to the present invention, the resulting image scan after $XeF_2$ treatment to remove implanted Ga and after deposition of the high quality oxide layer, results in a clear steady-state voltage contrast image of the n-well vs. p-substrate regions. FIG. 7a is a voltage contrast image, showing n-well regions 120 and p-substrate regions 122. FIG. 7b is the corresponding CAD layout, clearly showing the equivalence.

Experimental results using the heat and heat/UV treatment of step 85 have shown voltage contrast from buried structures such as poly dummies and depletion regions starting at about 5 microns above the buried structures. When the silicon above the n-well is sufficiently thin, poly gates below the diffusion regions within the n-well have also been observed.

Figure 7C:
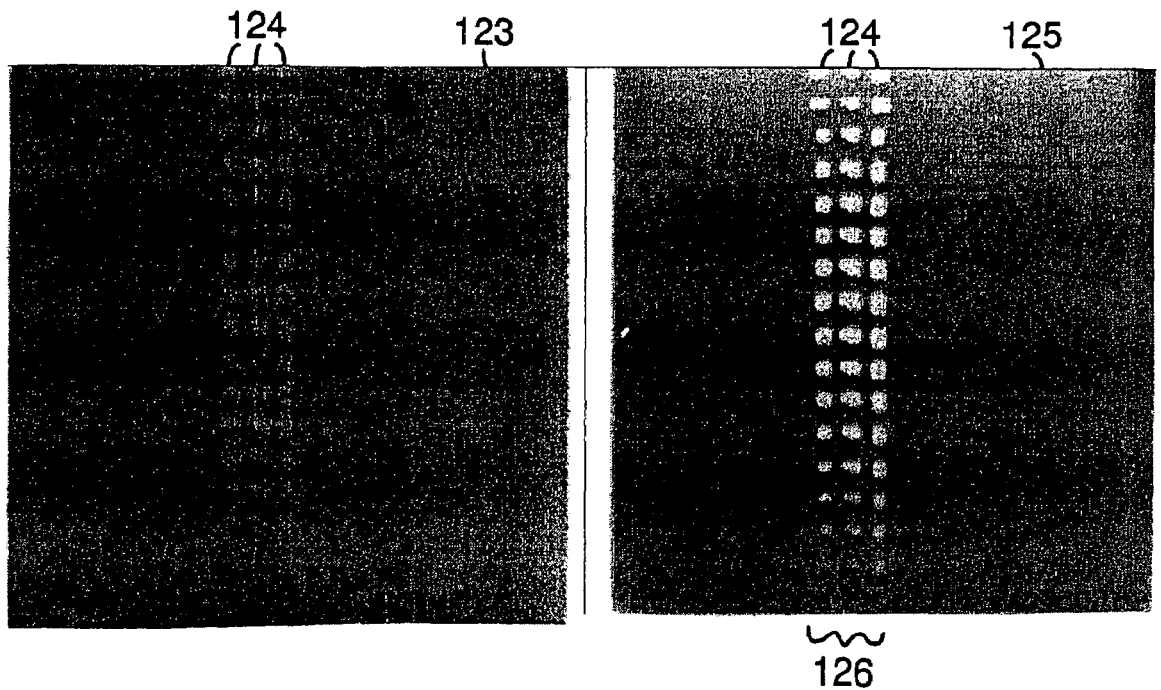
FIG. 7c is a comparison of voltage contrast with and without heat/UV treatment.

FIG. 7c shows the improvement in voltage contrast image following heat/UV treatment. Whereas VC image 123 without heat treatment shows n-wells 124 only, VC image 125 with heat/UV for 5 hours at 70-80 degrees shows enhanced voltage contrast of n-wells 124, and additionally reveals buried dummy poly 126. Pure UV treatment without heat is found to increase voltage contrast up to 2.5 hours treatment, then to decrease it. This is thought to be due to the initial neutralization of the oxide film by generated photo-electrons, followed by the creation of net negative charge which would again decrease the voltage contrast. Pure in-situ heat treatment without UV also is found to increase voltage contrast and sharpen the image for treatment up to 30 minutes, then stays approximately level for treatment up to about 5 hours, as well as revealing buried structures. It is also believed that low temperature imaging after oxide deposition and the aforementioned heat/UV anneal will yield favorable results, due to the changing of charging/discharging dynamics.

Buried structures such as the buried poly shown in FIG. 7c are also revealed upon a process known as "Pt reveal", which comprises performing an in-situ FIB-activated Pt deposition. This method is used for observing voltage contrast on a Silicon On Insulator (SOI) structure. An embodiment of this method comprises introducing 1 to $3\times10^{-5}$ Torr of methylcyclopentadienyl(trimethyl) platinum for about 20 seconds over a large area, resulting in a deposited Pt layer of less than 5 nm thickness. The alignment between the Fib and the CAD can be performed without the optical image for SOI devices where the oxide is exposed. The different materials underneath presumably change the potential on the oxide surface by some capacitive effect. First a small Pt layer is deposited, and then it is etched with EDI. The Pt is removed at different rates depending presumably on that surface potential. The underneath structure is then revealed. The contrast is high because there are two surface materials with opposite secondary electron emission: oxide and grounded Pt.

Figure 7D:
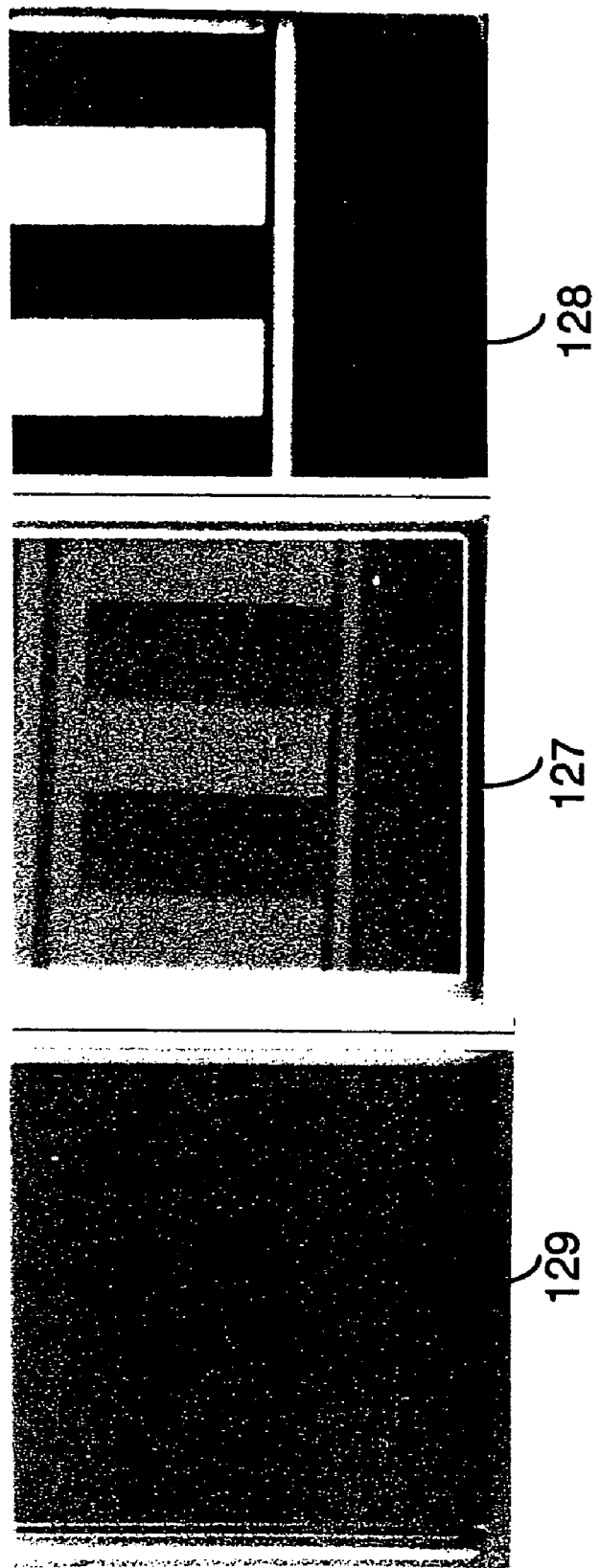
FIG. 7d is a comparison of voltage contrast with and without IR illumination during oxide deposition.

FIG. 7d shows an improvement in voltage contrast due to illumination during oxide deposition. This is in contrast to the improvement shown in FIG. 7c, which results from heat/UV treatment following oxide deposition. The results reported herein were achieved using IR illumination (wherein the IR illumination and the FIB beam are operating simultaneously during oxide deposition), but it is expected that illumination at other wavelengths such as visible or UV will produce a similar effect. The images shown are of oxide film deposited at 6 keV energy, 0.1 pA/um² current density, over equivalent n-well structures. Imaging conditions are 6 nA current, magnification of 2. VC image 127 results from no illumination during in-situ FIB oxide deposition. The oxide resistance in this case is measured as $55\times10^5$ ohms-cm, and the voltage contrast value is measured as 13.6%. VC image 128 results from illumination during in-situ FIB oxide deposition at 70% of maximum intensity, at wavelength centered at 1 um, using a 1 um filter with bandwidth of 70 nm. The oxide resistance in this case is measured as $15\times10^5$ Ohms-cm, and the voltage contrast value is measured as 80%. In comparison, a PVD ex-situ deposited film yields VC image 129. Voltage contrast is very low, about 1.5%, and film resistance is higher than either of the in-situ FIB deposited films (on the order of $10^{10}$ ohms-cm). It is expected that other types of ex-situ deposited films such as CVD will yield similar results. The data shown in FIG. 7d is believed to be indicate an inverse relation between oxide resistance and voltage contrast, and to also indicate a decrease in oxide resistance with illumination during oxide deposition.

Figure 8:
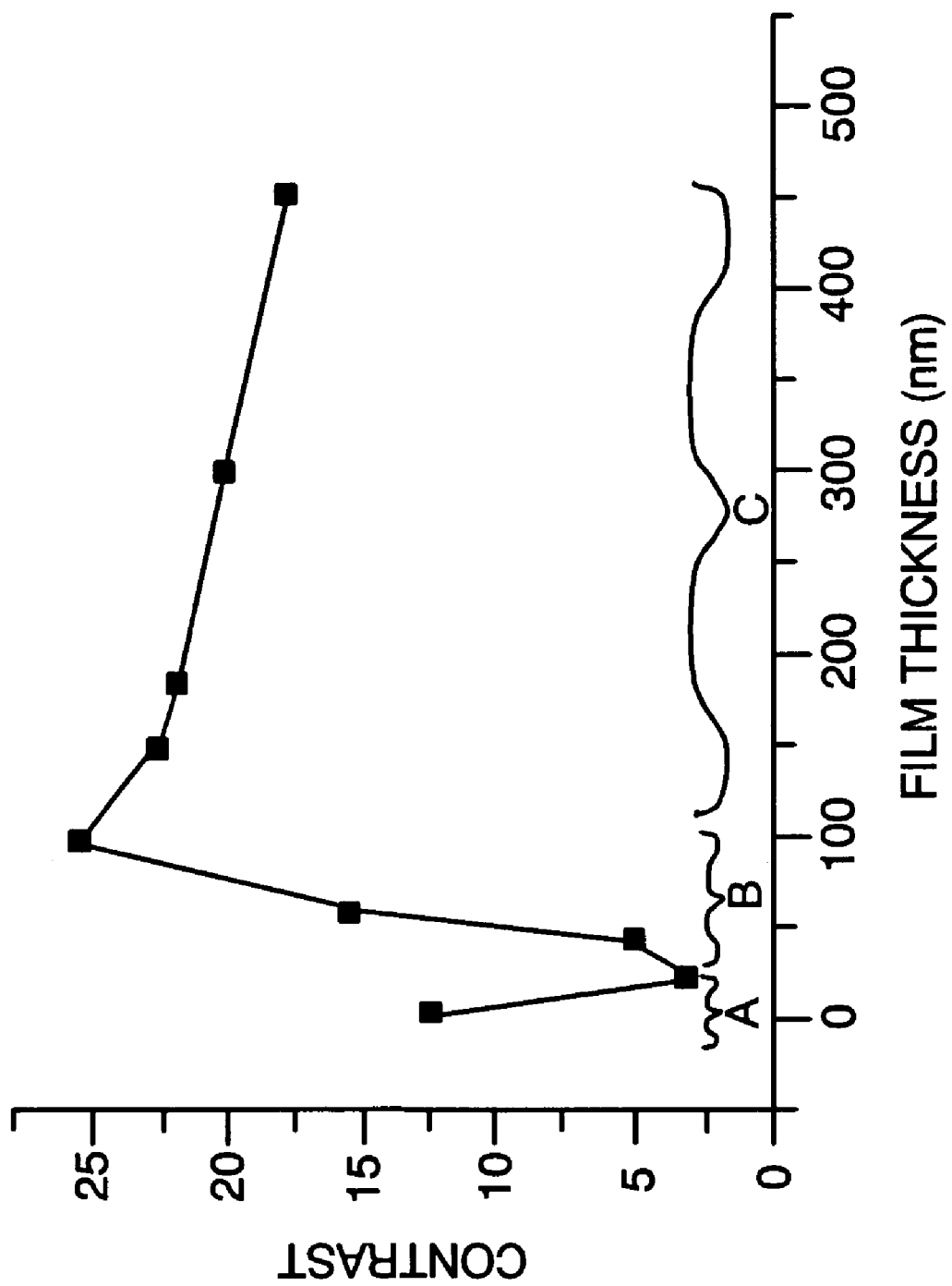
FIG. 8 is a graph of voltage contrast vs. oxide thickness for imaging beam energy of 30 keV.

FIG. 8 is a graph of voltage contrast vs. thickness of the oxide film, for imaging beam energy of 30 keV. Voltage contrast between the p-substrate and the n-well is defined as $$C = \frac{100 |I_{sub} - I_{well}|}{I_{sub} + I_{well}}$$

where $I_{sub}$ and $I_{well}$ are secondary emission from p-substrate and n-well regions respectively. Region A is dark, and the image becomes bright in regions B and C. The minimum value of contrast occurs at about 30 nm film thickness for 30 KeV beam shown in the figure. A similar graph results for beam energy of 15 keV, and the minimum contrast occurs at about 15 nm thickness for 15 keV beam. These values are believed to correspond to the concentration peak for implanted gallium at these energies. The maximum voltage contrast occurs in the range between 100 and 150 nm film thickness for both beam energies. However, oxide thicknesses in the range between 60 nm and greater than one micron have yielded significant voltage contrast.

Figure 9:
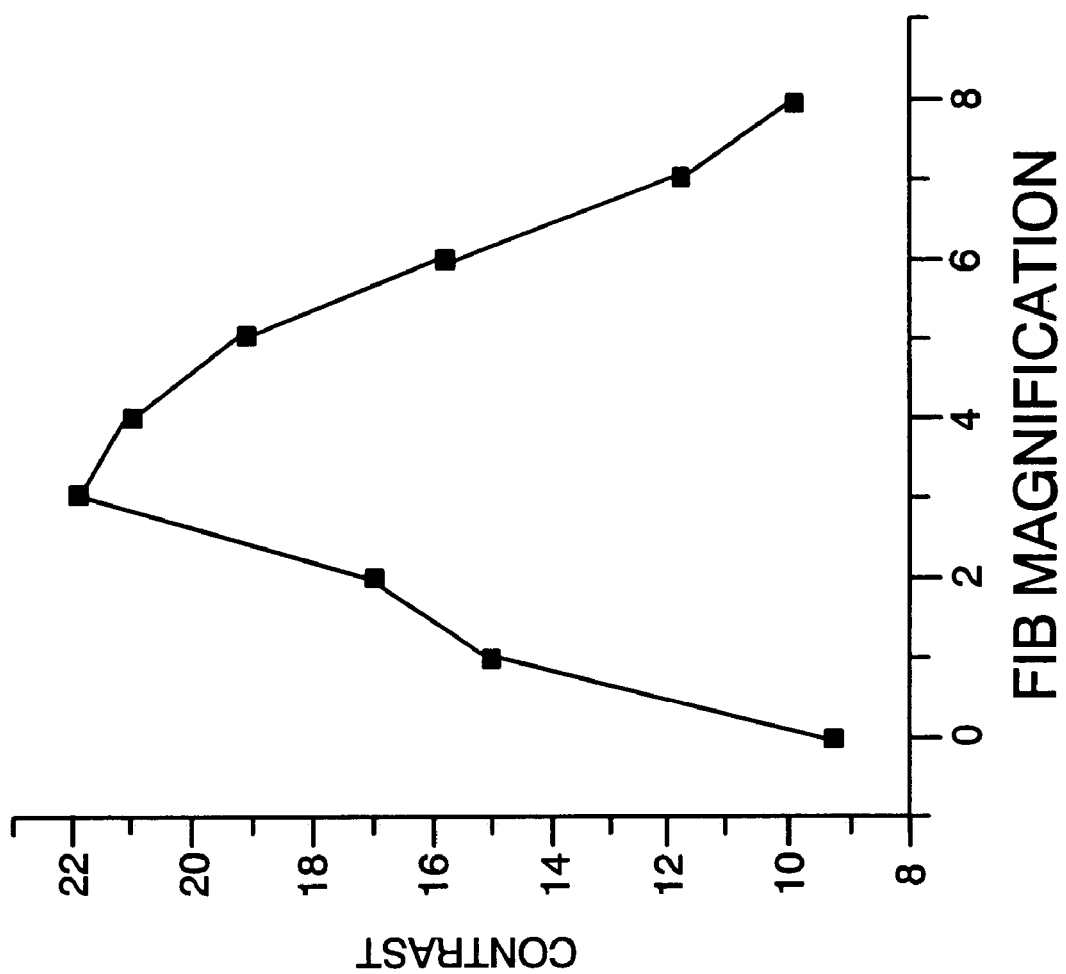
FIG. 9 is a graph of voltage contrast vs. FIB magnification during imaging, following oxide deposition.

FIG. 9 is a graph of voltage contrast vs. FIB magnification during FIB imaging, following 130 nm oxide deposition. Higher magnification corresponds to a smaller field of view and therefore a higher average beam current density for constant beam current. Beam current in this case was held at 1 nA. It is seen that the voltage contrast is maximum for magnification in the range between 3 and 4, corresponding to an average beam current density of about 5-40 nA/square micron. It is believed that the contrast dependence on beam current density correlates to the contrast being enhanced when a specific dose of Ga is implanted at a location in the oxide film. It is believed that increasing the beam current density above optimal values floods the insulator surface with positively charged Ga ions and forms a conductive sheet which degrades the contrast. Too low a beam current density is believed to decrease the potential difference between different regions and lower the secondary emission current. A discussion of these mechanisms is found in E. L. Cole, "Beam-Based Localization Techniques for IC Failure Analysis", *Microelectronic Failure Analysis, Desk Reference* 4th ed., R. Ross, C. Boit, D Staab, editors (2001) ASM International, Materials Park, Ohio, pages 136-137.

Figure 10:
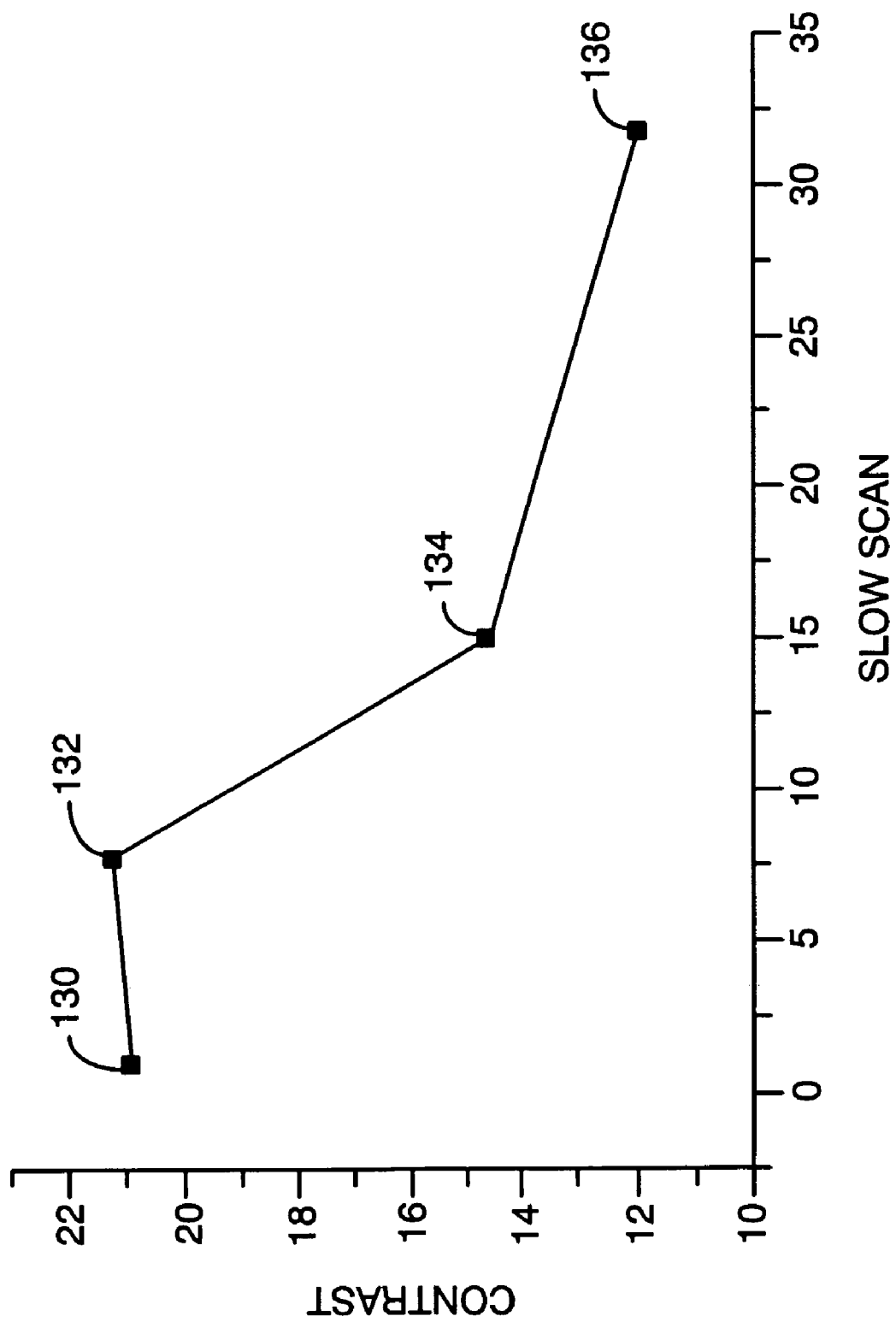
FIG. 10 is a graph of voltage contrast as a function of scan rate, after oxide deposition.

FIG. 10 is a graph of voltage contrast as a function of scan rate for 130 nm oxide deposition, with the x-axis representing factor of reduction in scan rate, with an initial value of 60 hz. Point 130 is scanned at 60 hz, point 132 at 60/8=8.5 hz, point 134 at 60/16=4.25 hz, and point 136 at 60/32=2.125 hz. Voltage contrast is seen to remain high at 8.5 hz, but to decrease sharply between 8.5 hz and 4.25 hz. The scan speed is proportional to the integrated beam current density, with a slower scan speed having a higher integrated beam current density, and thereby putting down a charge per unit area at a higher rate. It is seen that down to 8.5 hz, the leakage through the oxide layer, the trench wall, and other leakage paths can dissipate the accumulated positive charge from Ga ions between scans.

The highest imaging voltage contrast at for Field of View (FOV)=182×172 um occurs at 12 nA beam current. However, for alignment purposes, a much lower field of view is preferred, about 50 um squared. For this FOV, the image voltage contrast is the same for beam currents of 1,2,4, and 6 nA. The preferred beam current at this FOV is 1 nA, since the beam is less destructive at this value.

Figure 11:
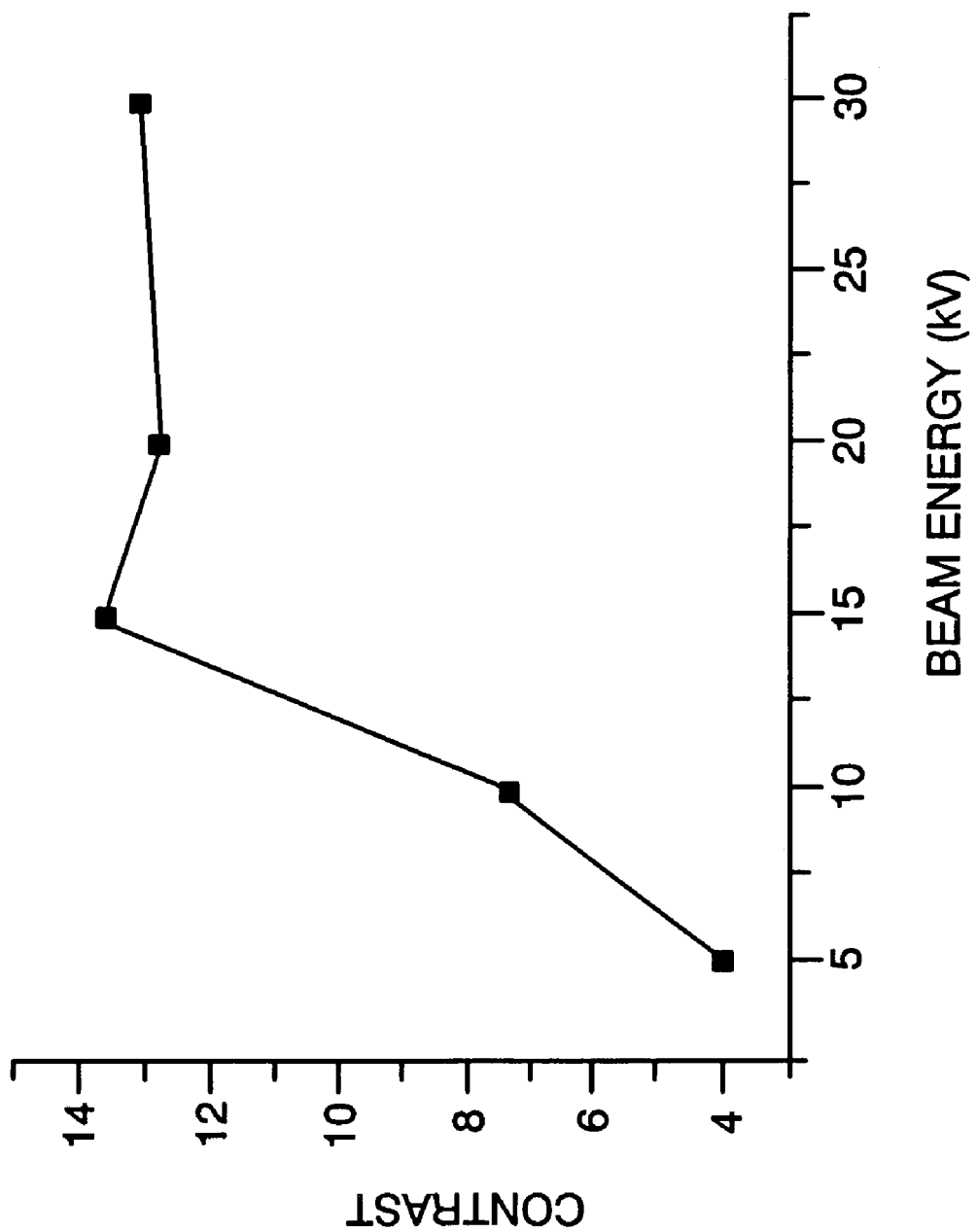
FIG. 11 is a graph of voltage contrast vs. imaging FIB beam energy after oxide deposition.

FIG. 11 is a graph of voltage contrast as a function of imaging FIB beam energy for 130 nm oxide deposition. Contrast is maximized at 15 keV, but remains high for beam energies as high as 30 keV, and greatly decreases for beam energies of 5 and 10 keV. In addition, a 15 keV FIB beam is easier to calibrate than a 10 keV beam, therefore the optimum energy range for the imaging FIB beam is 15-30 keV. Imaging beam current values range between 500 pA-20 nA.

Figure 12:
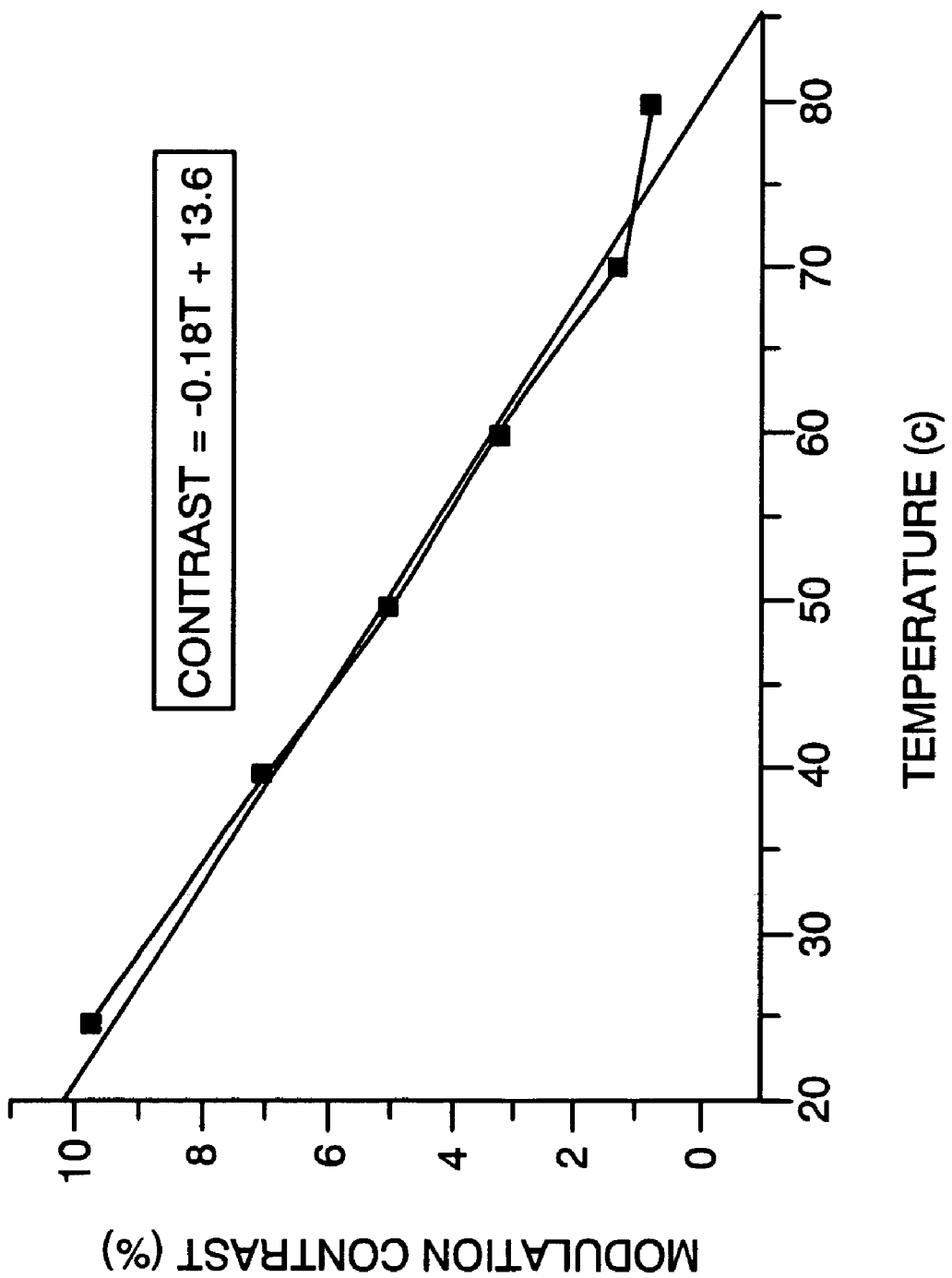
FIG. 12 is a graph of voltage contrast vs. imaging temperature.

FIG. 12 is a graph of voltage contrast as a function of imaging temperature. It is seen that contrast decreases linearly with respect to temperature. The linear relation has been calculated to be Contrast=−.18T+13.6, where T is the temperature in degrees C. By way of example, at T=25 C (room temperature), the capacitive voltage contrast of the imaged sample is 9.1.

Step 92 comprises aligning the FIB image with the CAD layout, and navigating to the precise location for milling of the fine FIB trench to access the desired circuit element. An embodiment of the alignment procedure is as follows:

1. CAD-OptiFIB 3-point alignment using the die corner
2. High beam current (500 pA-6 nA) and 10 pA alignment on a drawn fiducial mark (cross)
3. Local FIB-CAD alignment using VC at high beam current (>1 nA)
4. Switch to low BC (5-50 pA) and make a fiducial on the edit location
5. Switch to the high BC again, and realign the FIB to the CAD
6. Measure at high BC the offset between the cross and the edit location
7. Switch to low BC and place the box, i.e. mark the right location for the software, to electrically deflect the FIB beam to the edit location according to the measured offset An alternate embodiment of the alignment procedure is:

Following the CAD-OptiFIB 3-point alignment, use a voltage contrast image to locally align the CAD to the FIB at a beam current between 250 pA to 4 nA, place the target location in the center of the Field of View, and mark the surface exactly in the center by forming a spot (with the Focused Ion Beam with no dynamic deflection for a short period of time, usually 100 ms), lower the FIB beam current and configure the software to direct the FIB beam at the target location.

Step 94 comprises milling the fine FIB trench to the circuit location being edited. This method is described in "*FIB Techniques to Debug Flip-Chip ICs*", by R. Livengood et al, Semiconductor International, March 1998, pg. 111.

Proposed Mechanisms

It is believed that the initial appearance of a transient voltage contrast as the n-well is encountered (using sufficiently low beam energy, along with $XeF_2$ chemistry during milling, to minimize the implanted Ga layer) is a direct materials contrast, wherein the higher electron donor doping density of the n-well region compared to the p-substrate produces a higher secondary electron yield. The n-well therefore appears brighter than the p-substrate. During imaging scans, when the $XeF_2$ flow is halted, Ga is implanted into the surface layer of both the n-well and the p-substrate. This creates a kind of p-doped surface, which, atop the n-well only, results in a p-n junction. Due to the thinness of the implanted Ga (30-60 nm) compared with the n-well thickness (about 1-2 um), the doping characteristics are those of a one-sided or hyperabrupt junction. A depletion region is formed at the junction, depleting the surface region of the n-well of mobile carriers, and lowering the secondary electron yield. Thus the n-well region becomes dark as the Ga is implanted atop the n-well.

A suggested mechanism for the creation of a steady state voltage contrast upon removal of the surface Ga layer and deposition of an oxide layer is as follows:

After removal of the surface Ga layer by the $XeF_2$ treatment, the n-well regions are bright, according to the materials contrast described above. As the oxide layer is deposited, the n-well region is dark for very thin oxide thickness (see FIG. 8, Region A). It is believed that in Region A the oxide thickness is less than the Ga implantation depth, and that therefore an ohmic contact exists through the oxide. The resulting depletion region as described above causes the n-well region to be dark compared with the p-substrate.

In Region B, FIG. 8, the voltage contrast changes to yield bright n-well regions. It is believed that the dark-to-bright transition occurs as the oxide thickness increases past the gallium implantation depth, the ohmic-like contact is broken, and capacitive effects begin to dominate. The presence of the FIB deposited oxide atop the semiconductor substrate, with the addition of the Induced Surface Conductive Layer (ISCL) created by the Ga ion beam, produces an MOS capacitor with a positive electrode at the top. It is proposed that the voltage contrast in this region is a Capacitive Coupling Voltage Contrast (CCVC):

Since the image is induced by a scanning FIB beam, the oxide layer acts as the dielectric of a discharging capacitor, with a dynamic signal, to generate an image of changing subsurface voltages. The scanning Ga ion beam will cause a net positive charge to build up on the surface. In addition, a bound surface charge will be produced at the ISCL when structures below the maximum beam penetration depth change potential, and the intervening material becomes polarized. The CCVC signal is the change in secondary electron yield caused by this bound potential. The contrast in CCVC images is modulated by the time constant, i.e., the time the surface of the RC circuit takes to reach equilibrium. Insulator quality (for example the insulator resistance as shown in FIG. 7d, wherein a lower insulator resistance correlates to higher VC) and leakage paths will influence the RC time constant.

Figure 13:
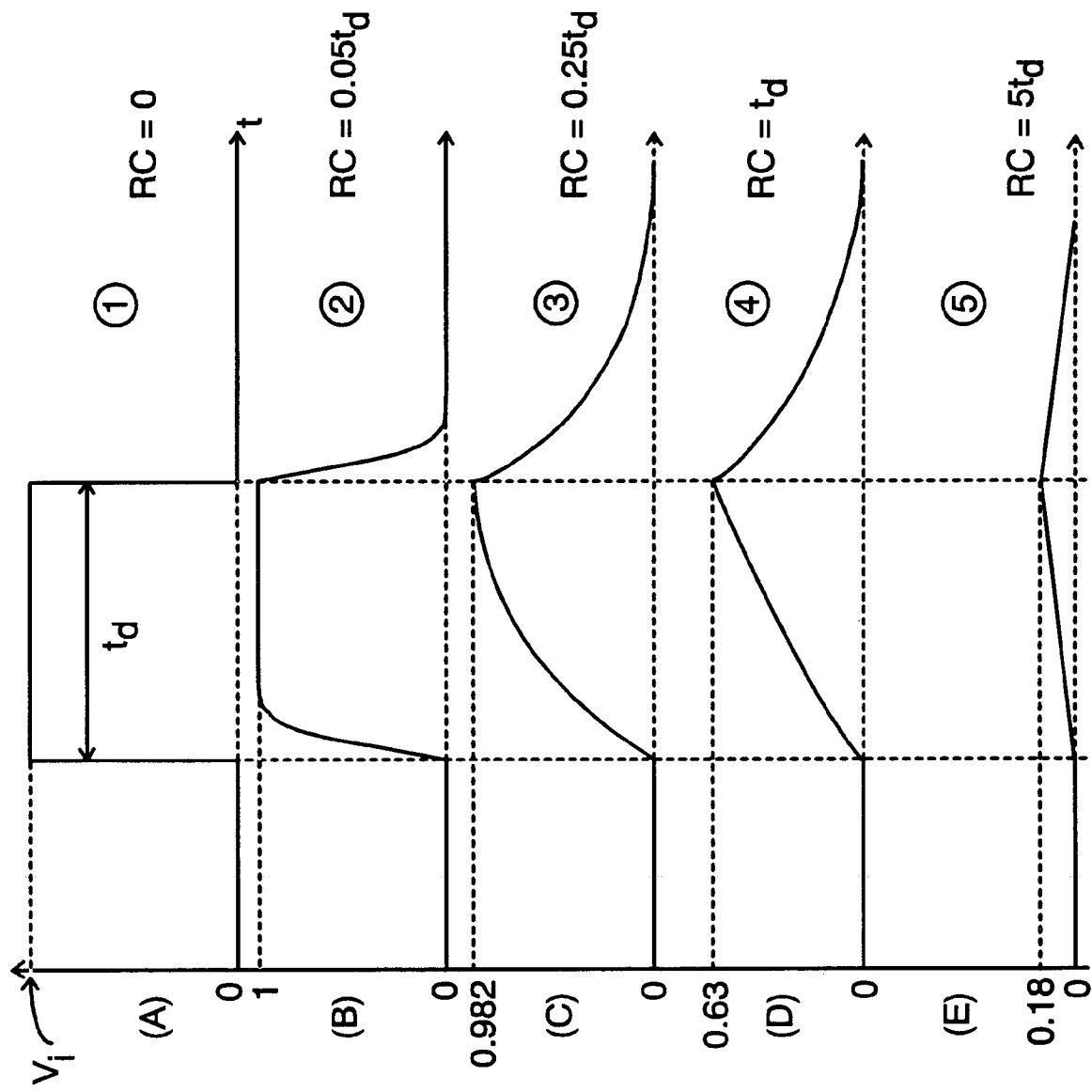
FIG. 13 is an illustration of induced surface voltage from a single scan of a FIB beam as a function of time, for range of RC time constants.

FIG. 13 illustrates the induced surface voltage from a single scan of the FIB beam as a function of time, for a range of RC time constants. Curve (a) shows induced surface voltage $V_i$ vs. t for RC=0, for a scan pulse of duration $t_2$ (during which secondary electrons are collected). The induced voltage is square in form, with voltage reaching a maximum value instantly, and discharging to zero voltage instantly as the scan pulse terminates. Curves (b)-(e) show the induced voltage as the RC time constant increases. The maximum amplitude of the induced voltage signal decreases, and discharge time increases.

It is believed that, since the n-well region is more heavily doped than the p-substrate, the capacitor above the n-well region will have a smaller RC time constant, and will therefore charge and discharge faster than that above the p-substrate. The p-substrate region will not fully discharge from one ion beam imaging scan pulse before the next pulse occurs, and therefore a positive charge will build up over the p-substrate, which will then appear dark on the image.

Buried structures have also been seen by voltage contrast, particularly after heat/UV treatment. This is believed to be due to their longer-range effect on the capacitive characteristics at the surface, according to a series capacitance structure.

Using the method disclosed herein, we have been able to produce a steady state voltage contrast FIB image of a FIB-milled trench floor. The image is present without sample biasing (every pin on the device is grounded), and requires no additional equipment or fixturing. N-well vs p-substrate contrast has been imaged, as well as buried dummy poly, and depletion regions between active n- and p-regions outside wells. The inventive method enables a simple, non-destructive, and accurate alignment of an integrated circuit die with the CAD layout to permit editing and other modifications to the circuit.

Figure 14A:
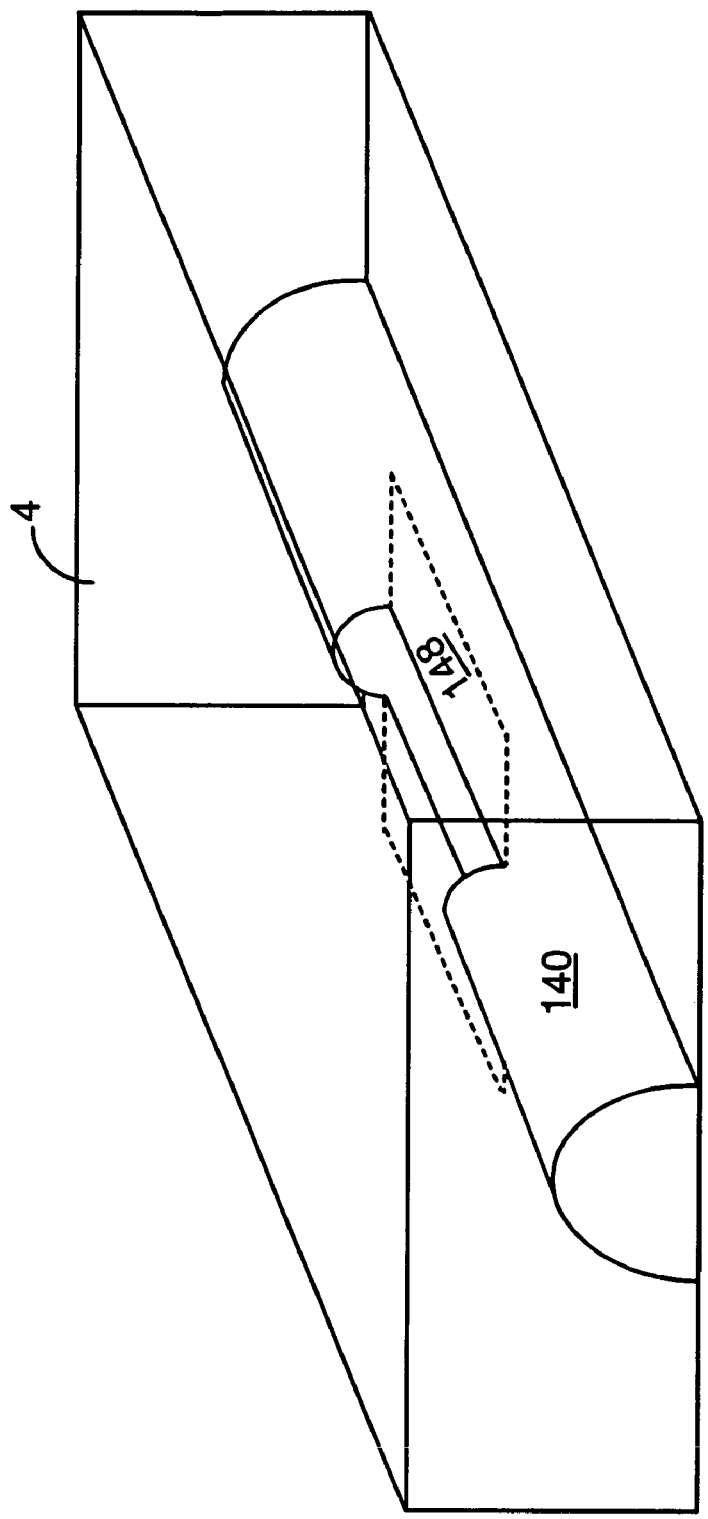
FIG. 14a illustrates a first method for employing the present invention to provide vertical doping profile information.
Figure 14B:
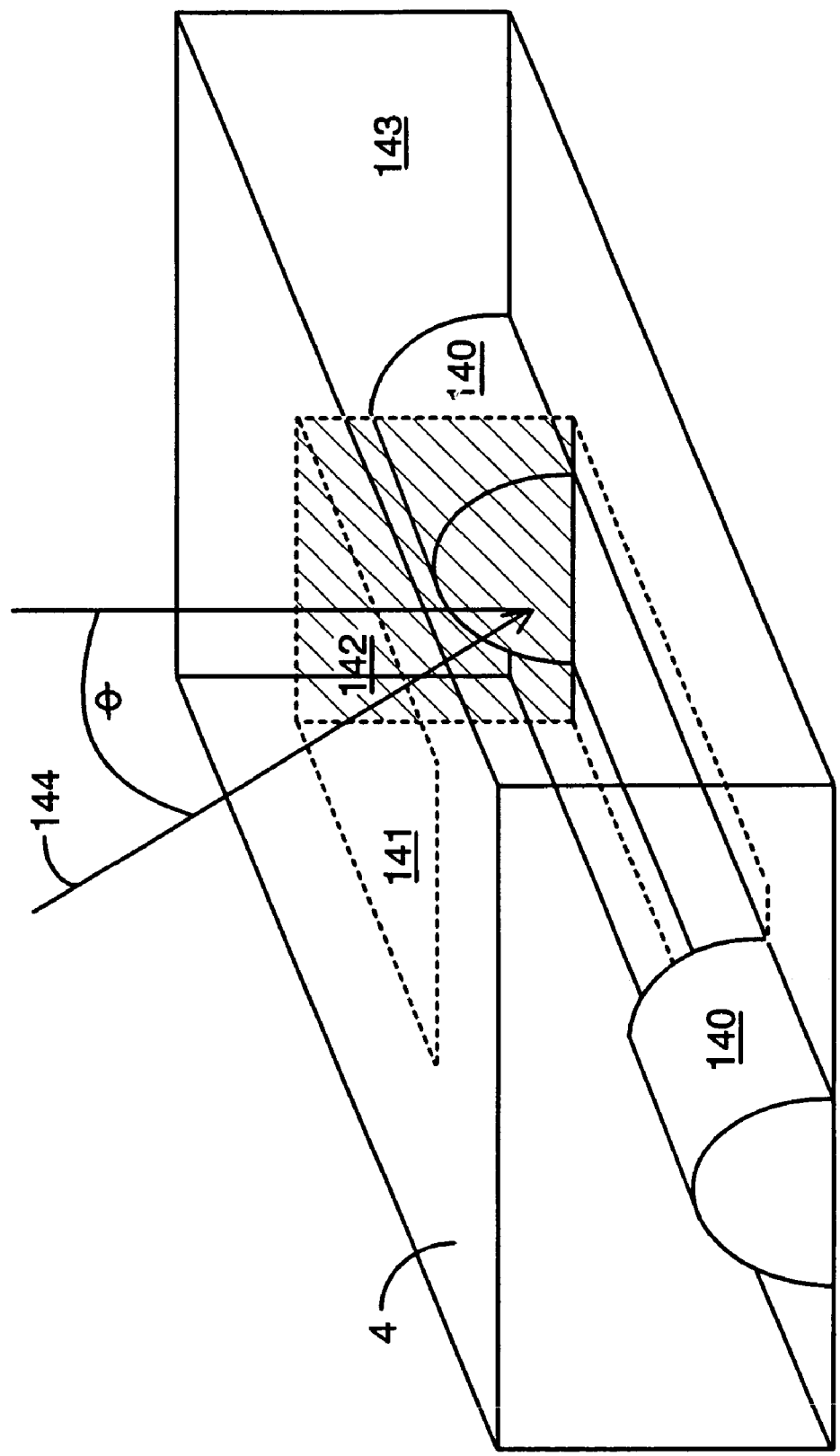
FIG. 14b illustrates a second method for employing the present invention to provide vertical doping profile information.
Figure 14C:
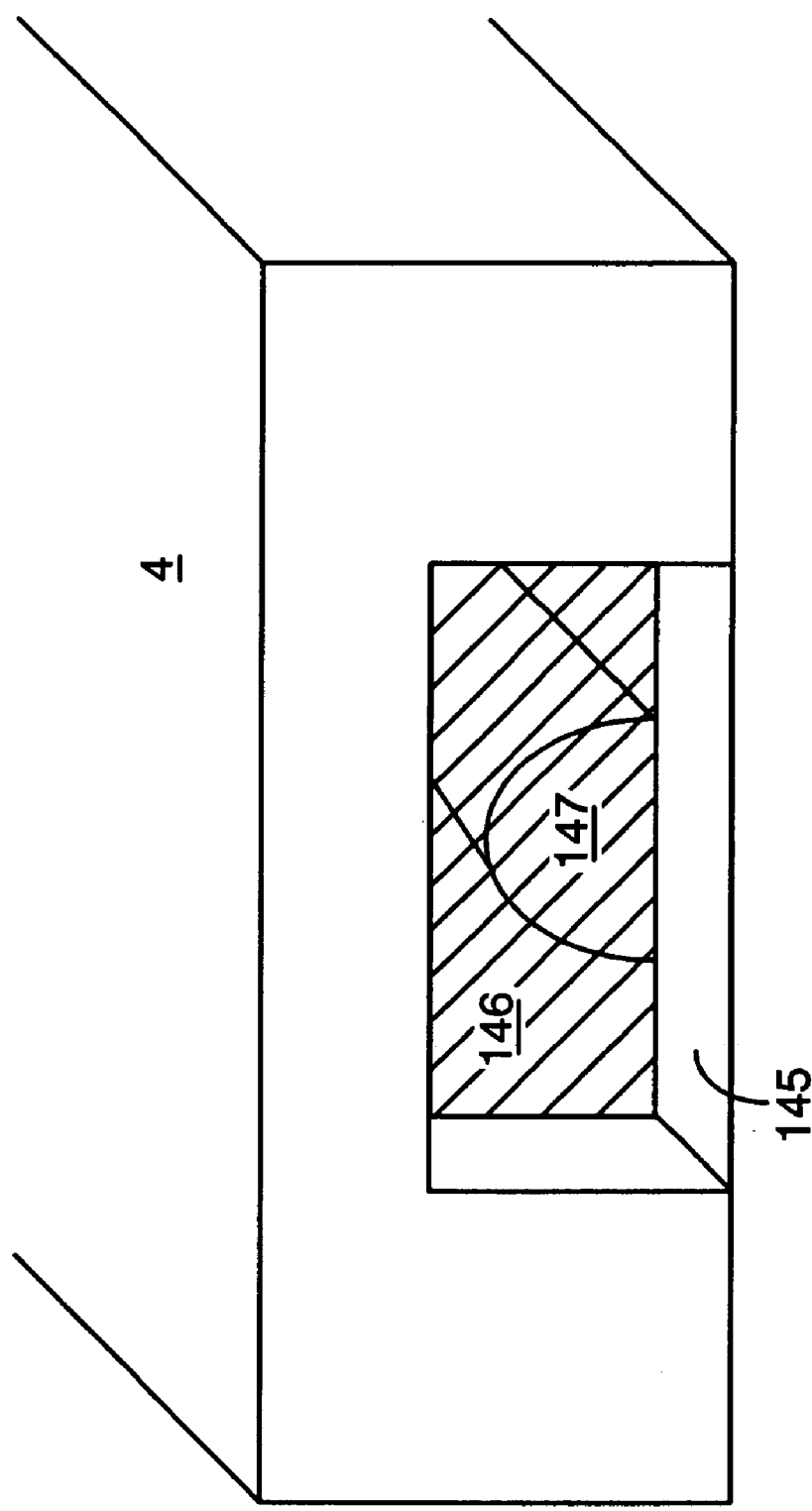
FIG. 14c illustrates a third method for employing the present invention to provide vertical doping profile information.

The method can also be used to provide vertical doping profile information, in one of several ways:

1) (illustrated in FIG. 14a) by indicating the position and size of a doped region 140 at intervals, using imaging according to the methods of the present invention, as the ion beam mills vertically through the region (the milled region 148 would necessarily encompass the doped region in at least one horizontal dimension);

2) (illustrated in FIG. 14b) by milling a vertical trench 141 all the way through the doped region 140, the milled trench encompassing the doped region in at least one horizontal dimension, such that one of the trench sidewalls 142 forms a vertical cross section near enough to the doped region to observe voltage contrast between the doped region and the surrounding region 143; then forming a non-transient voltage contrast on that trench sidewall encompassing the doped region, using the methods of the present invention, and imaging the trench sidewall using a tilted beam 144 (the trench would need to be in the range of 1-3 times wider than it is deep to enable viewing of the side wall at an angle between 70 and 45 degrees from normal);

3) (illustrated in FIG. 14c) by milling a horizontal trench 145 through a cross section of the wafer portion, the trench having a bottom surface 146 which encompasses the vertical doped region 147, until the bottom trench surface reaches the doped region, then imaging the trench bottom at the doped region using the methods of the present invention to form a non-transient voltage contrast.

System Considerations "

Figure 15:
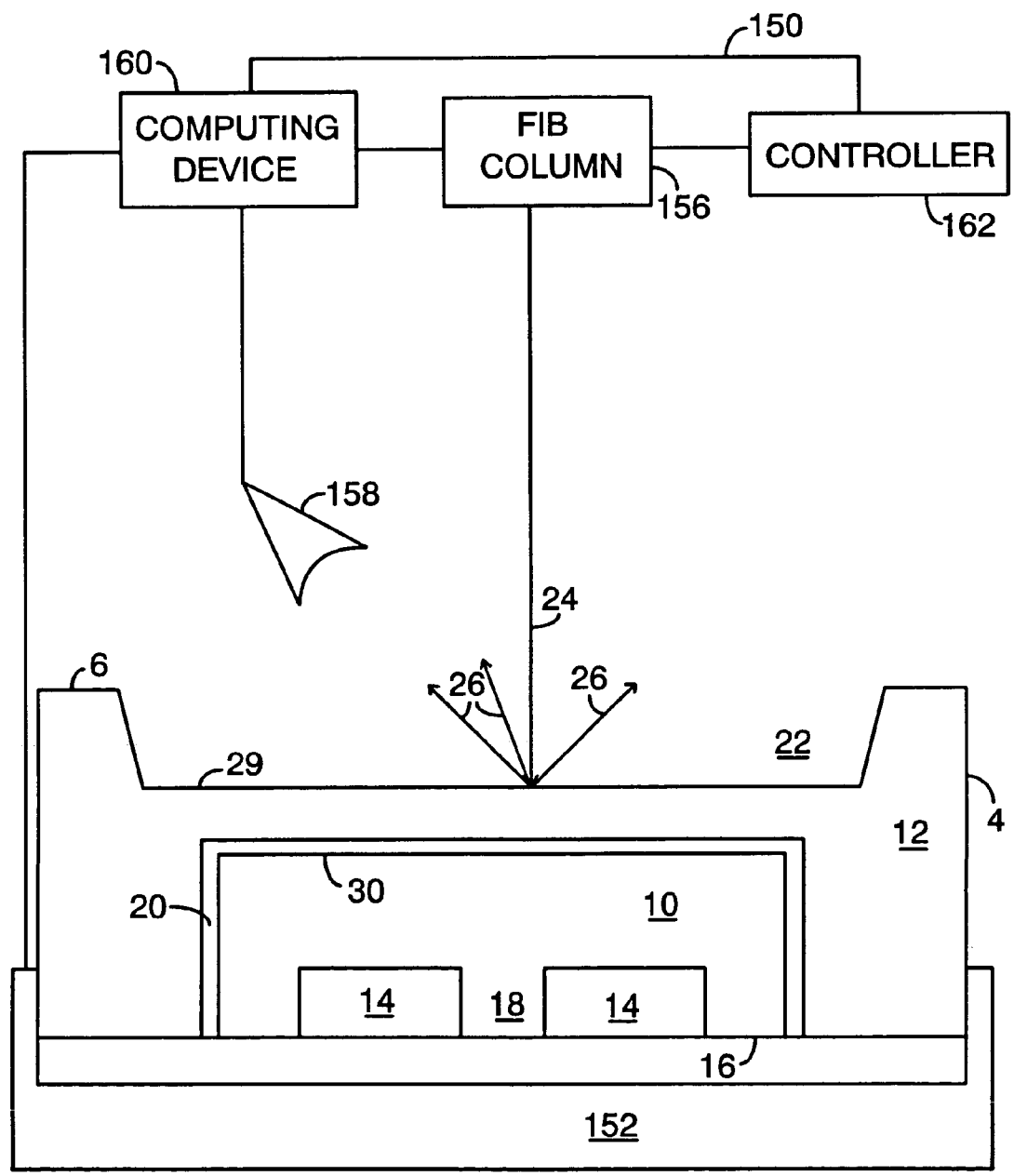
FIG. 15 is a schematic diagram of an exemplary system for implementing the inventive method.

The method described herein can be implemented in one embodiment using a FIB system 150, which is illustrated in FIG. 15. The system includes sample holder 152, FIB column 156, detector 158, computing device 160, and one or more controllers 162, as well as optional thinning devices and thickness measurement devices. A description of these system components is found in previously cited U.S. patent application Ser. No. 10,274,431 by C.C. Tsao et al. In another embodiment, which includes UV and/or heat treatment of the sample, the system must include either in-situ or ex-situ heat and/or light sources." The computing device includes a computer-readable storage medium containing stored data such as: the image of the wafer portion, and CAD information pertaining to the corresponding wafer portion."

It is to be understood that the invention described herein is not restricted to the exact embodiments described. Changes and modifications may be made without departing from the inventive concept. By way of example, the methods described can be employed with any charged particle beam, such as electron beam or ion beams of species other than Ga. The invention is further not restricted to use in backside editing: the improved quality of the insulator deposited as described herein can be used for frontside or backside circuit editing to isolate and protect exposed conductors physically, electrically, and chemically. The scope of the invention is to be construed in view of the claims.

With this in mind, we claim:

1. A wafer portion probing system comprising:
at least one grounding connection to ground said wafer portion;
a charged particle beam column configured to generate a charged particle beam that, when directed at a location on a surface of an integrated circuit wafer portion, generates secondary electrons;
a detector configured to detect said secondary electrons;
an image generator configured to generate, based on an output of said detector, an inherent voltage contrast image of regions within said surface of said wafer portion;
a computing device configured to navigate, based on said image, to a specified location on said wafer portion; and
a source of at least one of: light and heat, for substantially uniformly exposing said wafer portion thereto in situ.

2. The wafer portion probing system of claim 1 wherein said computing device is further configured to control circuit editing by said charged particle beam at said specified location on said wafer portion.

3. The system of claim 1, wherein said computing device is further configured to control at least a portion of
a method of establishing a non-transient voltage contrast between a first doped region and a second doped region in said wafer portion, said wafer portion having a first surface and a second surface opposite said first surface;
said wafer portion having a first semiconductor surface region of said second surface directly atop said first doped region, and having a second semiconductor surface region of said second surface directly atop said second doped region, said voltage contrast being observable on a charged particle beam image of said wafer portion, the method comprising the steps of:
installing said wafer portion in a vacuum chamber in a charged particle beam apparatus;
etching said first semiconductor surface region and said second semiconductor surface region with an etch chemistry for a first time period, for removing an implanted material-containing portion of said first semiconductor surface region and said second semiconductor surface region;
following said first time period, depositing an insulator layer atop said etched first semiconductor surface region and said etched second semiconductor surface region; and
forming an image of said first doped region and said second doped region from secondary electrons emitted from said first and said second doped region, said first doped region being externally unbiased electrically from said second doped region.

4. The system of claim 3, wherein said computing device is further configured to control at least a portion of the steps of:
ion milling a deep trench with the charged particle beam prior to the step of etching said first semiconductor surface region and said second semiconductor surface region, with an etch chemistry for a first time period;
wherein said charged particle beam is a Focused Ion Beam (FIB), and
wherein the step of ion milling a deep trench with the focused ion beam comprises milling until a contrast between said first and second doped regions is seen on said image.

5. The system of claim 4, wherein said computing device is further configured to control the utilizing of an etch assist chemistry to assist said ion milling of a deep trench.

6. The system of claim 5, wherein said etch assist chemistry comprises XeF2.

7. The system of claim 6, wherein said computing device is further configured to control the flowing of said XeF2 at a first flow rate during said ion milling step to maintain a first partial chamber pressure of XeF2, and wherein said computing device is configured to control said step of etching said first semiconductor surface region and said second semiconductor surface region with an etch chemistry for a first time period for removing an implanted material-containing portion of said first semiconductor surface region and said, second semiconductor surface region, wherein said step of etching said first semiconductor surface region and said second semiconductor surface region with an etch chemistry for a first time period for removing an implanted material-containing portion of said first semiconductor surface region and said second semiconductor surface region comprises:

continuing said flowing of said XeF2 at a second flow rate to maintain a second partial chamber pressure of XeF2 for a second time period while discontinuing said ion milling with said Focused Ion Beam; then discontinuing said flowing of said XeF2.

8. The system of claim 3, wherein said etch assist chemistry comprises XeF2, and wherein said computing device is configured to control said step of etching said first semiconductor surface region and said second semiconductor surface region with an etch chemistry for a first time period for removing an implanted material-containing portion of said first semiconductor surface region and said second semiconductor surface region, wherein said step of etching said first semiconductor surface region and said second semiconductor surface region with an etch chemistry for a first time period for removing an implanted material-containing portion of said first semiconductor surface region and said second semiconductor surface region comprises:

flowing said XeF2 at a flow rate to maintain a partial chamber pressure of XeF2 for a time period; then discontinuing said flowing of said XeF2.

9. The system of claim 3, wherein said computing device is further configured to control at least a portion of the steps of:

depositing said insulator layer in situ by said charged particle beam, wherein said insulator layer comprises silicon oxide.

10. The system of claim 9, wherein said charged particle beam is selected from the group consisting of: Focused Ion Beam (FIB) and electron beam.

11. The system of claim 3, wherein said computing device is further configured to control the step of exposing said wafer portion to at least one of the group consisting of heat and UV light following insulator deposition to enhance said voltage contrast.

12. The system of claim 3, wherein said computing device is further configured to control the step of illuminating said wafer portion during insulator deposition.

13. The system of claim 12, wherein said illuminating comprises illumination selected from the group consisting of: IR, visible, and UV wavelengths.

14. The system of claim 13, wherein said illuminating comprises IR illumination operating simultaneously with said charged particle beam.

15. The system of claim 1 further including a thinning device for thinning said wafer portion.

16. The system of claim 15 wherein said thinning device is a silicon-etching laser.

17. The wafer probing system of claim 1 further including a thickness measurement device for measuring the thickness of said wafer portion.

18. The system of claim 1 wherein said charged particle beam column is a focused ion beam column.

19. The system of claim 1 including a light source.

20. The system of claim 19 wherein said light source is IR.

21. The system of claim 19 wherein said light source is in-situ.

22. The system of claim 1 including a heat source.

23. The system of claim 22 wherein said heat source is in-situ.

24. The system of claim 22 wherein said heat source is ex-situ.

25. The system of claim 1 wherein said source of at least one of:

light and heat includes a UV source.

* * * * *